(12) United States Patent
Caban et al.

(10) Patent No.: US 11,672,983 B2
(45) Date of Patent: Jun. 13, 2023

(54) SENSOR IN CLOTHING OF LIMBS OR FOOTWEAR

(71) Applicant: ONWARD MEDICAL N.V., Eindhoven (NL)

(72) Inventors: Miroslav Caban, Eindhoven (NL); Niek Borgers, Eindhoven (NL); Urs Keller, Eindhoven (NL); Joachim von Zitzewitz, Eindhoven (NL); Jurriaan Bakker, Eindhoven (NL); Vincent Delattre, Eindhoven (NL); Robin Brouns, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 0 days.

(21) Appl. No.: 16/682,942

(22) Filed: Nov. 13, 2019

(65) Prior Publication Data
US 2020/0147384 A1 May 14, 2020

(30) Foreign Application Priority Data

Nov. 13, 2018 (EP) .................................. 18205817

(51) Int. Cl.
*A61N 1/18* (2006.01)
*A61N 1/36* (2006.01)
(Continued)

(52) U.S. Cl.
CPC ....... *A61N 1/36031* (2017.08); *A61N 1/0484* (2013.01); *A61N 1/36003* (2013.01);
(Continued)

(58) Field of Classification Search
CPC .. A61B 5/4824; A61B 2505/09; A61N 1/3601
See application file for complete search history.

(56) References Cited

U.S. PATENT DOCUMENTS

| 2,868,343 | A | 1/1959 | Sproul |
| 3,543,761 | A | 12/1970 | Bradley |

(Continued)

FOREIGN PATENT DOCUMENTS

| CA | 2649663 A1 * | 11/2007 | ............... A61H 3/00 |
| CA | 2856202 A1 | 5/2013 | |

(Continued)

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Michael J D'Abreu
(74) *Attorney, Agent, or Firm* — Finnegan, Henderson, Farabow, Garrett & Dunner, LLP

(57) ABSTRACT

A control system for a movement reconstruction and/or restoration system for a patient, comprising a CNS-Stimulation Module, especially an EES-Module, configured and arranged to provide CNS-Stimulation to a patient, and/or a PNS-Stimulation Module, especially an FES-Module, configured and arranged to provide PNS-Stimulation to a patient, a controller configured and arranged to control the CNS-Stimulation Module and/or the PNS-Stimulation Module, and at least one sensor configured and arranged to measure at least one parameter indicative of the movement of at least one limb and/or part of a limb of a patient.

11 Claims, 12 Drawing Sheets

(51) Int. Cl.

| | | |
|---|---|---|
| *A61N 1/04* | (2006.01) | |
| *A61B 90/00* | (2016.01) | |
| *A61B 5/00* | (2006.01) | |
| *A61B 5/107* | (2006.01) | |
| *A61B 5/11* | (2006.01) | |
| *A61H 3/00* | (2006.01) | |
| *A63B 21/055* | (2006.01) | |
| *A61B 5/389* | (2021.01) | |

(52) U.S. Cl.
CPC .......... *A61B 5/0077* (2013.01); *A61B 5/1071* (2013.01); *A61B 5/1128* (2013.01); *A61B 5/389* (2021.01); *A61B 5/6807* (2013.01); *A61B 2090/065* (2016.02); *A61B 2090/066* (2016.02); *A61B 2562/0219* (2013.01); *A61B 2562/0223* (2013.01); *A61H 3/00* (2013.01); *A63B 21/0552* (2013.01)

(56) References Cited

U.S. PATENT DOCUMENTS

| | | |
|---|---|---|
| 3,650,277 A | 3/1972 | Sjostrand et al. |
| 3,653,518 A | 4/1972 | Polen |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,340,216 A | 7/1982 | Murphy |
| 4,356,902 A | 11/1982 | Murphy |
| 4,379,462 A | 4/1983 | Borkan et al. |
| 4,398,537 A | 8/1983 | Holmbo |
| 4,402,501 A | 9/1983 | Lohman |
| 4,410,175 A | 10/1983 | Shamp |
| 4,414,986 A | 11/1983 | Dickhudt et al. |
| 4,538,624 A | 9/1985 | Tarjan |
| 4,549,556 A | 10/1985 | Tarjan et al. |
| 4,569,352 A | 2/1986 | Petrofsky et al. |
| 4,574,789 A | 3/1986 | Forster |
| 4,724,842 A | 2/1988 | Charters |
| 4,742,054 A | 5/1988 | Naftchi |
| 4,784,420 A | 11/1988 | Makino |
| 4,798,982 A | 1/1989 | Voorman |
| 4,800,898 A | 1/1989 | Hess et al. |
| 4,934,368 A | 6/1990 | Lynch |
| 5,002,053 A | 3/1991 | Garcia-Rill et al. |
| 5,018,631 A | 5/1991 | Reimer |
| 5,031,618 A | 7/1991 | Mullet |
| 5,081,989 A | 1/1992 | Graupe et al. |
| 5,121,754 A | 6/1992 | Mullett |
| 5,337,908 A | 8/1994 | Beck, Jr. |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,421,783 A | 6/1995 | Kockelman |
| 5,441,465 A | 8/1995 | Hefner et al. |
| 5,562,718 A | 10/1996 | Palermo |
| 5,571,141 A | 11/1996 | Mcneil et al. |
| 5,601,527 A | 2/1997 | Selkowitz |
| 5,626,540 A | 5/1997 | Hall |
| 5,643,330 A | 7/1997 | Holsheimer et al. |
| 5,667,461 A | 9/1997 | Hall |
| 5,733,322 A | 3/1998 | Starkebaum |
| 5,788,606 A | 8/1998 | Rich |
| 5,819,962 A | 10/1998 | Okubo et al. |
| 5,876,425 A | 3/1999 | Gord et al. |
| 5,983,141 A | 11/1999 | Sluijter et al. |
| 5,988,933 A | 11/1999 | Wilhelmstatter et al. |
| 6,058,331 A * | 5/2000 | King .................. A61N 1/3605 607/2 |
| 6,066,163 A | 5/2000 | John |
| 6,104,957 A | 8/2000 | Alo et al. |
| 6,115,634 A | 9/2000 | Donders et al. |
| 6,122,548 A | 9/2000 | Starkebaum et al. |
| 6,139,475 A | 10/2000 | Bessler et al. |
| 6,182,843 B1 | 2/2001 | Tax et al. |
| 6,188,927 B1 | 2/2001 | Lu et al. |
| 6,236,892 B1 | 5/2001 | Feler |
| 6,281,207 B1 | 8/2001 | Richter et al. |
| 6,308,103 B1 | 10/2001 | Gielen |
| 6,309,401 B1 | 10/2001 | Redko et al. |
| 6,319,241 B1 | 11/2001 | King et al. |
| 6,464,208 B1 | 10/2002 | Smith |
| 6,470,213 B1 | 10/2002 | Alley |
| 6,516,227 B1 | 2/2003 | Meadows et al. |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,901,292 B2 | 5/2005 | Hrdlicka et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,135,497 B1 | 11/2006 | Zeman et al. |
| 7,146,221 B2 | 12/2006 | Krulevitch et al. |
| 7,149,773 B2 | 12/2006 | Haller et al. |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,330,760 B2 | 2/2008 | Heruth et al. |
| 7,337,005 B2 | 2/2008 | Kim et al. |
| 7,340,298 B1 | 3/2008 | Barbut |
| 7,377,006 B2 | 5/2008 | Genoa et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | de Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,769,464 B2 | 8/2010 | Geber et al. |
| 7,780,617 B2 | 8/2010 | Tornatore et al. |

(56) References Cited

U.S. PATENT DOCUMENTS

| | | |
|---|---|---|
| 7,797,057 B2 | 9/2010 | Harris |
| 7,801,600 B1 | 9/2010 | Carbunaru et al. |
| 7,801,601 B2 | 9/2010 | Maschino et al. |
| 7,813,803 B2 | 10/2010 | Heruth et al. |
| 7,813,809 B2 | 10/2010 | Strother et al. |
| 7,861,872 B2 | 1/2011 | Ng et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,063,087 B2 | 11/2011 | Chow et al. |
| 8,100,815 B2 | 1/2012 | Balaker et al. |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,239,038 B2 | 8/2012 | Wolf, II |
| 8,260,436 B2 | 9/2012 | Gerber et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,332,053 B1 | 12/2012 | Patterson et al. |
| 8,346,366 B2 | 1/2013 | Arle et al. |
| 8,352,036 B2 | 1/2013 | Dimarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,626,300 B2 | 1/2014 | Demarais et al. |
| 8,740,825 B2 | 6/2014 | Ehrenreich et al. |
| RE45,030 E | 7/2014 | Stevenson et al. |
| 8,768,481 B2 | 7/2014 | Lane |
| 8,805,542 B2 | 8/2014 | Tai et al. |
| 8,836,368 B2 | 9/2014 | Afshar et al. |
| 8,847,548 B2 | 9/2014 | Kesler et al. |
| 8,957,549 B2 | 2/2015 | Kesler et al. |
| 9,079,039 B2 | 7/2015 | Carlson et al. |
| 9,101,769 B2 | 8/2015 | Edgerton et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,314,630 B2 | 4/2016 | Levin et al. |
| 9,358,384 B2 | 6/2016 | Dubuclet |
| 9,421,365 B2 | 8/2016 | Sumners et al. |
| 9,592,358 B2 | 3/2017 | Miller et al. |
| 9,597,517 B2 | 3/2017 | Moffitt |
| 9,717,908 B2 | 8/2017 | Karunasiri |
| 9,802,052 B2 | 10/2017 | Marnfeldt |
| 9,812,875 B2 | 11/2017 | Nejatali et al. |
| 9,895,545 B2 | 2/2018 | Rao et al. |
| 10,406,366 B2 | 9/2019 | Westlund et al. |
| 10,449,371 B2 | 10/2019 | Serrano Carmona |
| 10,799,701 B2 | 10/2020 | Lee |
| 10,806,935 B2 | 10/2020 | Sun et al. |
| 2002/0052539 A1 | 5/2002 | Haller et al. |
| 2002/0055779 A1 | 5/2002 | Andrews |
| 2002/0111661 A1 | 8/2002 | Cross et al. |
| 2002/0115945 A1 | 8/2002 | Herman et al. |
| 2002/0123672 A1 | 9/2002 | Christophersom et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0097166 A1 | 5/2003 | Krulevitch et al. |
| 2003/0113725 A1 | 6/2003 | Small et al. |
| 2003/0114894 A1 | 6/2003 | Dar et al. |
| 2003/0114899 A1 | 6/2003 | Woods et al. |
| 2003/0135253 A1 | 7/2003 | Kokones et al. |
| 2003/0145759 A1 | 8/2003 | Rodnunsky |
| 2004/0044380 A1 | 3/2004 | Bruninga et al. |
| 2004/0121528 A1 | 6/2004 | Krulevitch et al. |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Balzer et al. |
| 2004/0192082 A1 | 9/2004 | Wagner et al. |
| 2004/0192834 A1 | 9/2004 | Nakayoshi et al. |
| 2004/0243204 A1 | 12/2004 | Maghrib et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0075693 A1 | 4/2005 | Toy et al. |
| 2005/0090756 A1 | 4/2005 | Wolf et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Saavedra Barrera et al. |
| 2005/0239612 A1 | 10/2005 | Keiser |
| 2005/0246004 A1 | 11/2005 | Cameron et al. |
| 2005/0277999 A1 | 12/2005 | Strother et al. |
| 2006/0015153 A1 | 1/2006 | Gliner et al. |
| 2006/0041295 A1 | 2/2006 | Osypka |
| 2006/0089696 A1 | 4/2006 | Olsen et al. |
| 2006/0100671 A1 | 5/2006 | De Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0189453 A1 | 8/2006 | Leblond |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2007/0004567 A1 | 1/2007 | Shetty et al. |
| 2007/0009968 A1 | 1/2007 | Cunningham |
| 2007/0016097 A1 | 1/2007 | Farquhar et al. |
| 2007/0016329 A1 | 1/2007 | Herr et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0083240 A1 | 4/2007 | Peterson et al. |
| 2007/0100389 A1 | 5/2007 | Jaax et al. |
| 2007/0142874 A1 | 6/2007 | John |
| 2007/0142878 A1 | 6/2007 | Krulevitch et al. |
| 2007/0150023 A1 | 6/2007 | Ignagni et al. |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0233204 A1 | 10/2007 | Lima et al. |
| 2007/0265691 A1 | 11/2007 | Swanson |
| 2007/0293910 A1 | 12/2007 | Strother et al. |
| 2008/0009927 A1 | 1/2008 | Vilims |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0077192 A1 | 3/2008 | Harry et al. |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0221653 A1 | 9/2008 | Agrawal et al. |
| 2008/0228250 A1 | 9/2008 | Mironer |
| 2008/0234791 A1 | 9/2008 | Arle et al. |
| 2008/0269854 A1 | 10/2008 | Hegland et al. |
| 2008/0275129 A1 | 11/2008 | Lundstedt et al. |

(56) References Cited

U.S. PATENT DOCUMENTS

| | | |
|---|---|---|
| 2008/0287268 A1 | 11/2008 | Hidler et al. |
| 2008/0294211 A1 | 11/2008 | Moffitt |
| 2008/0294226 A1 | 11/2008 | Moffitt |
| 2008/0318733 A1 | 12/2008 | Osler-Weppenaar |
| 2009/0112281 A1 | 4/2009 | Miyazawa et al. |
| 2009/0204173 A1 | 10/2009 | Zhao et al. |
| 2009/0254151 A1 | 10/2009 | Anderson et al. |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2009/0312165 A1 | 12/2009 | Rempe |
| 2010/0004715 A1 | 1/2010 | Fahey |
| 2010/0006737 A1 | 1/2010 | Colombo et al. |
| 2010/0010646 A1 | 1/2010 | Drew et al. |
| 2010/0023103 A1 | 1/2010 | Elborno |
| 2010/0070010 A1 | 3/2010 | Simpson |
| 2010/0087782 A1 | 4/2010 | Ghaffari et al. |
| 2010/0114205 A1 | 5/2010 | Donofrio et al. |
| 2010/0116526 A1 | 5/2010 | Arora et al. |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0179562 A1 | 7/2010 | Linker et al. |
| 2010/0185253 A1 | 7/2010 | Dimarco et al. |
| 2010/0217355 A1 | 8/2010 | Tass et al. |
| 2010/0228310 A1 | 9/2010 | Shuros et al. |
| 2010/0241191 A1 | 9/2010 | Testerman et al. |
| 2010/0274312 A1 | 10/2010 | Alataris et al. |
| 2010/0280570 A1 | 11/2010 | Sturm et al. |
| 2010/0312304 A1 | 12/2010 | York et al. |
| 2011/0009919 A1 | 1/2011 | Carbunaru et al. |
| 2011/0029044 A1 | 2/2011 | Hyde et al. |
| 2011/0034912 A1 | 2/2011 | De Graff et al. |
| 2011/0034977 A1 | 2/2011 | Janik et al. |
| 2011/0054567 A1 | 3/2011 | Lane et al. |
| 2011/0054568 A1 | 3/2011 | Lane et al. |
| 2011/0054570 A1 | 3/2011 | Lane |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0016081 A1 | 6/2011 | Griffith |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224753 A1 | 9/2011 | Palermo et al. |
| 2011/0224757 A1 | 9/2011 | Zdeblick et al. |
| 2011/0230747 A1 | 9/2011 | Rogers et al. |
| 2011/0230808 A1 | 9/2011 | Lisowski |
| 2011/0237921 A1 | 9/2011 | Askin et al. |
| 2011/0260126 A1 | 10/2011 | Willis |
| 2012/0006793 A1 | 1/2012 | Swanson |
| 2012/0016448 A1 | 1/2012 | Lee |
| 2012/0016453 A1 | 1/2012 | Feler et al. |
| 2012/0018249 A1 | 1/2012 | Mehr |
| 2012/0035684 A1 | 2/2012 | Thompson et al. |
| 2012/0041518 A1 | 2/2012 | Kim et al. |
| 2012/0059432 A1 | 3/2012 | Emborg et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0116476 A1 | 5/2012 | Kothandaraman |
| 2012/0123293 A1 | 5/2012 | Shah et al. |
| 2012/0136408 A1 | 5/2012 | Grill et al. |
| 2012/0165899 A1 | 6/2012 | Gliner |
| 2012/0168397 A1 | 7/2012 | Lim et al. |
| 2012/0232615 A1 | 9/2012 | Barolat et al. |
| 2012/0271315 A1 | 10/2012 | Pianca et al. |
| 2012/0277834 A1 | 11/2012 | Mercanzini et al. |
| 2012/0330391 A1 | 12/2012 | Bradley et al. |
| 2013/0006793 A1 | 1/2013 | O'Sullivan et al. |
| 2013/0030501 A1 | 1/2013 | Feler et al. |
| 2013/0035745 A1 | 2/2013 | Ahmed et al. |
| 2013/0041235 A1 | 2/2013 | Rogers et al. |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0116604 A1 | 5/2013 | Morilla et al. |
| 2013/0116751 A1 | 5/2013 | Moffitt et al. |
| 2013/0123568 A1 | 5/2013 | Hamilton et al. |
| 2013/0138167 A1 | 5/2013 | Bradley et al. |
| 2013/0150915 A1 | 6/2013 | Kane et al. |
| 2013/0154373 A1 | 6/2013 | Lisuwandi et al. |
| 2013/0158444 A1 | 6/2013 | Herr et al. |
| 2013/0190143 A1 | 7/2013 | Greenhill et al. |
| 2013/0211477 A1 | 8/2013 | Cullen et al. |
| 2013/0253299 A1 | 9/2013 | Weber et al. |
| 2013/0253611 A1 | 9/2013 | Lee et al. |
| 2013/0268041 A1 | 10/2013 | Schulte et al. |
| 2013/0289664 A1 | 10/2013 | Johanek |
| 2013/0289667 A1 | 10/2013 | Wacnik et al. |
| 2013/0345780 A1 | 12/2013 | Tabada et al. |
| 2014/0005753 A1 | 1/2014 | Carbunaru |
| 2014/0058292 A1 | 2/2014 | Alford et al. |
| 2014/0074190 A1 | 3/2014 | Griffith |
| 2014/0087922 A1 | 3/2014 | Bayerlein et al. |
| 2014/0088674 A1 | 3/2014 | Bradley |
| 2014/0100491 A1 | 4/2014 | Hu et al. |
| 2014/0124713 A1 | 5/2014 | Majumdar et al. |
| 2014/0163640 A1 | 6/2014 | Edgerton et al. |
| 2014/0171961 A1 | 6/2014 | Lacey et al. |
| 2014/0172045 A1 | 6/2014 | Yip et al. |
| 2014/0172055 A1 | 6/2014 | Venancio |
| 2014/0180361 A1 | 6/2014 | Burdick et al. |
| 2014/0201905 A1 | 7/2014 | Glukhovsky |
| 2014/0228905 A1 | 8/2014 | Bolea |
| 2014/0243923 A1 | 8/2014 | Doan et al. |
| 2014/0277271 A1 | 9/2014 | Chan et al. |
| 2014/0316484 A1 | 10/2014 | Edgerton et al. |
| 2014/0316503 A1 | 10/2014 | Tai et al. |
| 2015/0012061 A1 | 1/2015 | Chen |
| 2015/0032187 A1 | 1/2015 | Ranu et al. |
| 2015/0057717 A1 | 2/2015 | Wu et al. |
| 2015/0051674 A1 | 3/2015 | Blum et al. |
| 2015/0066111 A1 | 3/2015 | Blum et al. |
| 2015/0094791 A1 | 4/2015 | Edgell et al. |
| 2015/0151114 A1 | 6/2015 | Black et al. |
| 2015/0196241 A1 | 7/2015 | Yekutieli |
| 2015/0217120 A1 | 8/2015 | Nandra et al. |
| 2015/0224326 A1 | 8/2015 | Toth et al. |
| 2015/0231396 A1 | 8/2015 | Burdick et al. |
| 2015/0320632 A1 | 11/2015 | Vallery et al. |
| 2015/0328462 A1 | 11/2015 | Griffith |
| 2015/0343199 A1 | 12/2015 | Wechter et al. |
| 2016/0001096 A1 | 1/2016 | Mishelevich |
| 2016/0005538 A1 | 1/2016 | Koyanagi et al. |
| 2016/0030748 A1 | 2/2016 | Edgerton et al. |
| 2016/0030750 A1 | 2/2016 | Bokil et al. |
| 2016/0121109 A1 | 5/2016 | Edgerton et al. |
| 2016/0136477 A1 | 5/2016 | Bucher et al. |
| 2016/0143588 A1 | 5/2016 | Hoitink et al. |
| 2016/0144167 A1 | 5/2016 | Bakker et al. |
| 2016/0144184 A1 | 5/2016 | Marnfeldt |
| 2016/0157389 A1 | 6/2016 | Hwang |
| 2016/0166828 A1 | 6/2016 | Yu |
| 2016/0175586 A1 | 6/2016 | Edgerton et al. |
| 2016/0220813 A1 | 8/2016 | Edgerton et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2016/0367827 A1 | 12/2016 | Tahmasian |
| 2017/0098962 A1 | 4/2017 | Desrosiers |
| 2017/0118722 A1 | 4/2017 | Hong et al. |
| 2017/0128729 A1 | 5/2017 | Netoff et al. |
| 2017/0157389 A1 | 6/2017 | Tai et al. |

(56) References Cited

U.S. PATENT DOCUMENTS

| | | |
|---|---|---|
| 2017/0157396 A1 | 6/2017 | Dixon et al. |
| 2017/0173326 A1 | 6/2017 | Bloch et al. |
| 2017/0266455 A1 | 9/2017 | Steinke |
| 2017/0348532 A1 | 12/2017 | Moffitt et al. |
| 2017/0354819 A1 | 12/2017 | Bloch et al. |
| 2017/0361093 A1 | 12/2017 | Yoo et al. |
| 2017/0361115 A1 | 12/2017 | Aghassian et al. |
| 2018/0056078 A1 | 3/2018 | Kashyap et al. |
| 2018/0083473 A1 | 3/2018 | Menegoli et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0133481 A1 | 5/2018 | Von Zitzewitz et al. |
| 2018/0153474 A1 | 6/2018 | Aeschlimann et al. |
| 2018/0178008 A1 | 6/2018 | Bouton et al. |
| 2018/0185648 A1 | 7/2018 | Nandra et al. |
| 2018/0193655 A1 | 7/2018 | Zhang et al. |
| 2018/0229038 A1 | 8/2018 | Burdick et al. |
| 2018/0236240 A1 | 8/2018 | Harkema et al. |
| 2018/0337547 A1 | 11/2018 | Menegoli et al. |
| 2018/0353755 A1 | 12/2018 | Edgerton et al. |
| 2018/0367187 A1 | 12/2018 | Mcfarthing |
| 2019/0160294 A1 | 5/2019 | Peterson et al. |
| 2019/0167980 A1 | 6/2019 | Petersen |
| 2019/0192864 A1 | 6/2019 | Koop et al. |
| 2019/0247680 A1 | 8/2019 | Mayer et al. |
| 2019/0269917 A1 | 9/2019 | Courtine et al. |
| 2019/0299006 A1 | 10/2019 | Marnfeldt |
| 2019/0344070 A1 | 11/2019 | Molnar et al. |
| 2019/0381313 A1 | 12/2019 | Lu |
| 2019/0381328 A1 | 12/2019 | Wechter et al. |
| 2020/0061378 A1 * | 2/2020 | Ganguly ............... A61N 1/0456 |
| 2020/0144846 A1 | 5/2020 | Shin |
| 2020/0228901 A1 | 7/2020 | Baek |
| 2021/0069052 A1 | 3/2021 | Burke |

FOREIGN PATENT DOCUMENTS

| | | | |
|---|---|---|---|
| CA | 2864473 A1 | 5/2013 | |
| CA | 3034123 A1 * | 2/2018 | ............ A61N 1/3603 |
| CA | 2823592 A1 | 11/2021 | |
| CN | 101227940 A | 7/2008 | |
| CN | 103263727 A | 8/2013 | |
| CN | 104307098 A | 1/2015 | |
| DE | 3830429 A1 | 3/1990 | |
| DE | 202007015508 U1 | 4/2008 | |
| DE | 102009055121 A1 | 6/2011 | |
| DE | 102015220741 A1 | 4/2017 | |
| EP | 0034145 A1 | 2/1981 | |
| EP | 0236976 A1 | 9/1987 | |
| EP | 1575665 A1 | 9/2005 | |
| EP | 1675648 A1 | 7/2006 | |
| EP | 1680182 A1 | 7/2006 | |
| EP | 2243510 A2 | 10/2010 | |
| EP | 2486897 A2 | 8/2012 | |
| EP | 2626051 A1 | 8/2013 | |
| EP | 2628502 A1 | 8/2013 | |
| EP | 2661307 A2 | 11/2013 | |
| EP | 2810689 A1 | 12/2014 | |
| EP | 2810690 A1 | 12/2014 | |
| EP | 2868343 A1 | 5/2015 | |
| EP | 2966422 A1 | 1/2016 | |
| EP | 3323466 A1 | 5/2018 | |
| EP | 3323468 A1 | 5/2018 | |
| EP | 3328481 A1 | 6/2018 | |
| EP | 3381506 A1 | 10/2018 | |
| EP | 3527258 A1 | 8/2019 | |
| JP | 3184145 B2 | 7/2001 | |
| JP | 2002200178 A | 7/2002 | |
| JP | 2008067917 A | 3/2008 | |
| KR | 101573840 B1 | 12/2015 | |
| RU | 2130326 C1 | 5/1999 | |
| RU | 2141851 C1 | 11/1999 | |
| RU | 2160127 C1 | 12/2000 | |
| RU | 2178319 C2 | 1/2002 | |
| RU | 2192897 C2 | 11/2002 | |
| RU | 2001102533 | 11/2002 | |
| RU | 2226114 C1 | 3/2004 | |
| RU | 2258496 C2 | 8/2005 | |
| RU | 2361631 C2 | 7/2009 | |
| RU | 2368401 C1 | 9/2009 | |
| RU | 2387467 C1 | 4/2010 | |
| RU | 2397788 C2 | 5/2010 | |
| RU | 2386995 C2 | 8/2010 | |
| RU | 2445990 C1 | 3/2012 | |
| RU | 2471518 C2 | 1/2013 | |
| RU | 2475283 C2 | 2/2013 | |
| WO | WO 199409808 | 5/1994 | |
| WO | WO 1997047357 A1 | 12/1997 | |
| WO | WO 199908749 | 2/1999 | |
| WO | 0234331 A2 | 5/2002 | |
| WO | WO 2002034331 A2 | 5/2002 | |
| WO | WO 2002092165 A1 | 11/2002 | |
| WO | WO 2003005887 A2 | 1/2003 | |
| WO | WO 2003026735 A2 | 4/2003 | |
| WO | WO 2003092795 A1 | 11/2003 | |
| WO | WO 2004087116 A2 | 10/2004 | |
| WO | WO 2005002663 A2 | 1/2005 | |
| WO | WO 2005051306 A2 | 6/2005 | |
| WO | WO 2005087307 A2 | 9/2005 | |
| WO | WO 2006026850 A1 | 3/2006 | |
| WO | 2007047852 A2 | 4/2007 | |
| WO | WO 2007057508 A1 | 5/2007 | |
| WO | WO 2007081764 A2 | 7/2007 | |
| WO | WO 2007107831 A2 | 9/2007 | |
| WO | WO 2008070807 A3 | 6/2008 | |
| WO | WO 2008075294 A1 | 6/2008 | |
| WO | WO 2008092785 A1 | 8/2008 | |
| WO | WO 2008109862 A2 | 9/2008 | |
| WO | WO 2008121891 A1 | 10/2008 | |
| WO | WO 2009042217 A1 | 4/2009 | |
| WO | WO 2009111142 A2 | 9/2009 | |
| WO | 2010021977 A1 | 2/2010 | |
| WO | WO 2010114998 A1 | 10/2010 | |
| WO | WO 2010124128 A1 | 10/2010 | |
| WO | WO 2011005607 A1 | 1/2011 | |
| WO | WO 2011008459 A2 | 1/2011 | |
| WO | WO 2011136875 A1 | 11/2011 | |
| WO | 2012080964 A1 | 6/2012 | |
| WO | WO 2012075195 A1 | 6/2012 | |
| WO | WO 2012094346 A2 | 7/2012 | |
| WO | WO 2012100260 A2 | 7/2012 | |
| WO | WO 2012129574 A2 | 9/2012 | |
| WO | WO 2013049658 A1 | 4/2013 | |
| WO | WO-2013069004 A1 * | 5/2013 | ............ A61B 5/0205 |
| WO | WO 2013071307 A1 | 5/2013 | |
| WO | WO 2013071309 A1 | 5/2013 | |
| WO | WO 2013117750 A1 | 8/2013 | |
| WO | WO 2013152124 A1 | 10/2013 | |
| WO | WO 2013179230 A1 | 12/2013 | |
| WO | WO 2014005075 A1 | 1/2014 | |
| WO | WO 2014031142 A1 | 2/2014 | |
| WO | WO 2014089299 A2 | 6/2014 | |
| WO | WO 2014144785 A1 | 9/2014 | |
| WO | WO 2014149895 A1 | 9/2014 | |
| WO | WO 2014205356 A2 | 12/2014 | |
| WO | WO 2014209877 A1 | 12/2014 | |
| WO | WO 2015000800 A1 | 1/2015 | |
| WO | WO-2015063127 A1 * | 5/2015 | ............ A61B 5/369 |
| WO | WO 2015106286 A1 | 7/2015 | |
| WO | WO 2015172894 A1 | 11/2015 | |
| WO | WO 2016029159 A2 | 2/2016 | |
| WO | WO 2016064761 A1 | 4/2016 | |
| WO | WO 2016110804 A1 | 7/2016 | |
| WO | WO 2016112398 A1 | 7/2016 | |
| WO | WO 2016172239 A1 | 10/2016 | |
| WO | 2017062508 A1 | 4/2017 | |
| WO | WO 2017058913 A1 | 4/2017 | |
| WO | WO 2017117450 A1 | 7/2017 | |
| WO | WO 2018039296 A2 | 3/2018 | |
| WO | WO-2018093765 A1 * | 5/2018 | ............ A61B 5/4848 |
| WO | WO 2012050200 A1 | 4/2019 | |
| WO | WO 2019211314 A1 | 11/2019 | |
| WO | WO 2020028088 A1 | 2/2020 | |

(56) References Cited

FOREIGN PATENT DOCUMENTS

OTHER PUBLICATIONS

Merrill, D. et al., "Electrical stimulation of excitable tissue: design of efficacious and safe protocols," Journal of Neuroscience Methods, vol. 141, No. 2, Feb. 15, 2005, 28 pages.
Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.
Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.
Van Den Brand, R. et al., "Restoring Voluntary Control of Locomotion after Paralyzing Spinal Cord Injury," Science, vol. 336, No. 6085, Jun. 1, 2012, 5 pages.
Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.
Levine, A. et al., "Identification of cellular node for motor control pathways," Nature Neuroscience, vol. 17, No. 4, Apr. 2014, Available Online Mar. 9, 2014, 22 pages.
Angeli, C. et al., "Altering spinal cord excitability enables voluntary movements after chronic complete paralysis in humans," BRAIN: A Journal of Neurology, vol. 137, No. 5, May 2014, Available Online Apr. 8, 2014, 16 pages.
Danner, S. et al., "Human spinal locomotor control is based on flexibly organized burst generators," BRAIN: A Journal of Neurology, vol. 138, No. 3, Mar. 2015, Available Online Jan. 12, 2015, 12 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.
Capogrosso, M. et al., "A Brain-Spinal Interface Alleviating Gait Deficits after Spinal Cord Injury in Primates," Nature, vol. 539, No. 7628, Nov. 10, 2016, 39 pages.
Miller, J. et al., "Parameters of Spinal Cord Stimulation and Their Role in Electrical Charge Delivery: A Review," Neuromodulation, vol. 19, No. 4, Jun. 2016, 12 pages.
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.
Anderson, K., "Targeting Recovery: Priorities of the Spinal Cord-Injured Population," Journal of Neurotrauma, vol. 21, No. 10, (Oct. 2004), 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Azimi, J. et al., "Batch Bayesian Optimization via Simulation Matching", In Advances in Neural Information Processing Systems (NIPS), (2010), 9 pages.

Azimi, J. et al., "Hybrid Batch Bayesian Optimization", In Proceedings of the 29th International Conference on Machine Learning, (2012), 12 pages.
Azimi, J. et al., "Batch Active Learning via Coordinated Matching", In Proceedings of the 29th International Conference on Machine Learning, (2012), 8 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, E. et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Dani, V. et al., "Stochastic Linear Optimization Under Bandit Feedback", In Proceedings of the 21st Annual Conference on Learning Theory (COLT), (2008), 15 pages.
Danner, S. M. et al., "Body Position Influences Which neural structures are recruited by lumbar transcutaneous spinal cord stimulation", PLoS ONE, vol. 11, No. 1, (2016), 13 pages.
Dimitrijevic, M. M. et al., "Evidence for a Spinal Central Pattern Generator in Humans", Annals New York Academy Sciences, vol. 860, (1998), pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.

(56) References Cited

OTHER PUBLICATIONS

Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.
Edgerton, V. et al., "Training Locomotor Networks," Brain Research Reviews, vol. 57, Published Online Sep. 16, 2007, (Jan. 2008), 25 pages.
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.
Ganley, K. J. et al., "Epidural Spinal Cord Stimulation Improves Locomotor Performance in Low ASIA C, Wheelchair-Dependent, Spinal Cord-Injured Individuals: Insights from Metabolic Response", Top. Spinal Cord Inj. Rehabil., vol. 11, No. 2, (2005), pp. 60-63.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harkema, S. et al., "Human Lumbosacral Spinal Cord Interprets Loading During Stepping," Journal of Neurophysiology, vol. 77, No. 2, (Feb. 1, 1997), 15 pages.
Harrison, P. et al., "Individual Excitatory Post-Synaptic Potentials Due to Muscle Spindle la Afferents in Cat Triceps Surae Motoneurones," The Journal of Physiology, vol. 312, No. 1, (Mar. 1981), pp. 455-470.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Herman, R. et al., "Spinal cord stimulation facilitates functional walking in a chronic, incomplete spinal cord injured," Spinal Cord, vol. 40, No. 2, (2002), 4 pages.
Hennig, P. et al., "Entropy search for information-efficient global optimization" Journal of Machine Learning Research (JMLR), vol. 13, (Jun. 2012), pp. 1809-1837.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
Jones, D. R. et al., "Efficient Global Optimization of Expensive Black-Box Functions", Journal of Global Optimization, vol. 13, (1998), pp. 455-492.
Kirkwood, P., "Neuronal Control of Locomotion: "From Mollusc to Man", G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metricspaces", In STOC, Computerand Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.
Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.
Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krause, A. et al. "Contextual Gaussian Process Bandit Optimization", In Advances in Neural Information Processing Systems (NIPS), (2011), 9 pages.

(56) References Cited

OTHER PUBLICATIONS

Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.

Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.

Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.

Liu, J. et al., "Stimulation of the Parapyramidal Region of the Neonatal Rat Brain Stem Produces Locomotor-Like Activity Involving Spinal 5-$HT_7$ and 5-$HT_{2A}$ Receptors", Journal of Neurophysiology, vol. 94, No. 2, Published Online May 4, 2005, (Aug. 1, 2005), 13 pages.

Lovely, R. et al., "Effects of Training on the Recovery of Full-Weight-Bearing Stepping in the Adult Spinal Cat," Experimental Neurology, vol. 92, No. 2, (May 1986), 15 pages.

Lozano, A. et al., "Probing and Regulating Dysfunctional Circuits Using Deep Brain Stimulation," Neuron, vol. 77, No. 3, (Feb. 6, 2013), 19 pages.

Lizotte, D. et al., "Automatic gait optimization with Gaussian process regression", In IJCAI, (2007), pp. 944-949.

McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.

Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.

Minassian, K. et al., "Peripheral and central afferent input to the lumbar cord", Biocybemetics and Biomedical Engineering, vol. 25, No. 3, (2005), pp. 11-29.

Minassian, K. et al., "Human lumbar cord circuitries can be activated by extrinsic tonic input to generate locomotor-like activity", Human Movement Science, vol. 26, No. 2, (2007), pp. 275-295.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.

Minassian, K. et al., "Neuromodulation of lower limb motor control in restorative neurology", Clinical Neurology and Neurosurgery, vol. 114, (2012), pp. 489-497.

Minassian, K. et al., "Mechanisms of rhythm generation of the human lumbar spinal cord in repose to tonic stimulation without and with step-related sensory feedback", Biomed Tech., vol. 58, (Suppl. 1), (2013), 3 pages.

Minev, I. R. et al., "Electronic dura mater for long-term multimodal neural interfaces," Science Magazine, vol. 347, No. 6218, (Jan. 9, 2015), 64 pages.

Minoux, M., Accelerated greedy algorithms for maximizing submodular set functions. Optimization Techniques, LNCS, (1978), pp. 234-243.

Murg, M et al., "Epidural electric stimulation of posterior structures of the human lumbar spinal cord: 1. Muscle twitches—a functional method to define the site of stimulation", Spinal Cord, vol. 38, (2000), pp. 394-402.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.

Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nandra, M. S. et al., "A parylene-based microelectrode array implant for spinal cord stimulation in rats", Conference Proceedings IEEE Eng. Med. Biol. Soc., (2011), pp. 1007-1010.

Nandra, M. S. et al., "A wireless microelectrode implant for spinal cord stimulation and recording in rats", Presentation Abstract, 2013.

Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.

Pearson, K. G., "Generating the walking gait: role of sensory feedback," Progress in Brain Research, vol. 143, Chapter 12, Published Online Nov. 28, 2003, (2004), 7 pages.

Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.

Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.

Pratt, G. et al., "Stiffness Isn't Everything," Proceedings of the Fourth International Symposium on Experimental Robotics, (Jun. 30, 1995), 6 pages.

Pratt, J. et al., "Series elastic actuators for high fidelity force control," Industrial Robot: An International Journal, vol. 29, No. 3, Available as Early as Jan. 1, 2002, (1995), 13 pages.

Prochazka, A. et al., "Ensemble firing of muscle afferents recorded during normal locomotion in cats," The Journal of Physiology, vol. 507, No. 1, (Feb. 15, 1998), 12 pages.

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning", The MIT Press, Cambridge, Massachusetts, (2006), 266 pages.

Rasmussen, C. E. et al., "Gaussian Processes for Machine Learning (GPML) Toolbox", The Journal of Machine Learning Research, vol. 11, (2010), pp. 3011-3015.

Rasmussen, C. E. "Gaussian Processes in Machine Learning", L.N.A.I., vol. 3176, (2003) pp. 63-71.

Rattay, F. et al., "Epidural electrical stimulation of posterior structures of the human lumbosacral cord: 2. Quantitative analysis by computer modeling", Spinal Cord, vol. 38, (2000), pp. 473-489.

Reinkensmeyer, D. et al., "Tools for understanding and optimizing robotic gait training", Journal of Rehabilitation Research & Development, vol. 43, No. 5, (Aug. 2006), 14 pages.

Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.

Robbins, H., "Some Aspects of the Sequential Design of Experiments", Bull. Amer. Math. Soc., vol. 58, (1952), pp. 527-535.

Rodger, D. C. et al., "High Density Flexible Parylene-Based Multielectrode Arrays for Retinal and Spinal Cord Stimulation",

(56) References Cited

OTHER PUBLICATIONS

Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Ryzhov, I. O. et al., "The knowledge gradient algorithm for a general class of online learning problems", Operations Research, vol. 60, No. 1, (2012), pp. 180-195.
Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.
Srinivas, N. et al., "Gaussian process optimization in the bandit setting: No regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007),16 pages.
Sun, F. et al., "Sustained axon regeneration induced by co-deletion of PTEN and SOCS3", Nature, vol. 480, No. 7377, Published Online Nov. 6, 2011, (Dec. 15, 2011),12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Vallery, H. et al., "Compliant Actuation of Rehabilitation Robots," IEEE Robotics & Automation Magazine, vol. 15, No. 3, (Sep. 12, 2008), 10 pages.
Wan, D. et al., "Life-threatening outcomes associated with autonomic dysreflexia: A clinical review," Journal of Spinal Cord Medicine, vol. 37, No. 1, Jan. 2014, 9 pages.
Ward, A. R., "Electrical Stimulation Using Kilohertz-Frequency Alternating Current", Physical Therapy, vol. 89, Published online Dec. 18, 2008, (2009), pp. 181-190.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.
Extended European Search Report and Written Opinion in counterpart European Application No. 18205817.2, dated Apr. 25, 2019, (5 pages).
Communication Pursuant to Article 94(3) EPC in counterpart European Application No. 18205817.2, dated Feb. 28, 2023, (1 page).

\* cited by examiner

| Fiber type | Diameter (μm) | Function |
|---|---|---|
| Ia (A-α) | 12-20 | Proprioception from muscle spindles |
| Ib (A-α) | 12-20 | Proprioception from Golgi tendon organs |
| II (A-β) | 5-12 | Fine touch, (2-point discrimination & vibration) |
| III (A-δ) | 2-5 | Light touch, fast pain & temperature |
| IV (C) | 0.5-1 | Slow pain & temperature |

Fig. 3

| # | FMB | Agonist | Antagonist |
|---|---|---|---|
| 1 | Right Ankle Extension | Right medial gastrocnemius, soleus | Right tibialis anterior |
| 2 | Right Ankle Flexion | Right tibialis anterior | Right medial gastrocnemius, soleus |
| 3 | Right Knee Extension | Right rectus femoris, vastus lateralis | Right iliopsoas, semitendinosus |
| 4 | Right Hip Extension | Right gluteus maximus, semitendinosus | Right iliopsoas, rectus femoris |
| 5 | Right Hip Flexion | Right iliopsoas, rectus femoris | Right gluteus maximus, semitendinosus |
| 6 | Right Trunk Stability | Right paraspinal muscles | |
| 7 | Left Ankle Extension | Left medial gastrocnemius, soleus | Left tibialis anterior |
| 8 | Left Ankle Flexion | Left tibialis anterior | Left medial gastrocnemius, soleus |
| 9 | Left Knee Extension | Left rectus femoris, vastus lateralis | Left iliopsoas, semitendinosus |
| 10 | Left Hip Extension | Left gluteus maximus, semitendinosus | Left iliopsoas, rectus femoris |
| 11 | Left Hip Flexion | Left iliopsoas, rectus femoris | Left gluteus maximus, semitendinosus |
| 12 | Left Trunk Stability | Left paraspinal muscles | |

Fig. 5

FMB/CMB used in Task 1

| Right | Left |
|---|---|
| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

FMB/CMB used in Task 2

| Right | Left |
|---|---|
| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

Fig. 6

SENSOR IN CLOTHING OF LIMBS OR FOOTWEAR

CROSS-REFERENCE TO RELATED APPLICATION

The present application claims priority to European Patent Application No. 18205817.2, filed on Nov. 13, 2018. The entire contents of the above-listed application is hereby incorporated by reference for all purposes.

TECHNICAL FIELD

The present invention relates to a system for controlling a movement reconstruction and/or restoration system for a patient, e.g. in the field of improving recovery after neurological disorders like spinal cord injury (SCI), for example after trauma.

BACKGROUND AND SUMMARY

Decades of research in physiology have demonstrated that the mammalian spinal cord embeds sensorimotor circuits that produce movement primitives (cf. Bizzi E. et al., *Modular organization of motor behavior in the frog's spinal cord. Trends in neurosciences* 18, 442-446 (1995); Levine A J. et al., Identification of a cellular node for motor control pathways. Nature neuroscience 17, 586-593, (2014)). These circuits process sensory information arising from the moving limbs and descending inputs originating from various brain regions in order to produce adaptive motor behaviours.

A spinal cord injury (SCI) interrupts the communication between the spinal cord and supraspinal centres, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf van den Brand R., et al., *Restoring Voluntary Control of Locomotion after Paralyzing Spinal Cord njury. Science* 336, 1182-1185 (2012); Angeli C A. et al., *Altering spinal cord excitability enables voluntary movements after chronic complete paralysis in humans. Brain: a journal of neurology* 137, 1394-1409 (2014); Harkema S. et al., *Effect of epidural stimulation of the lumbosacral spinal cord on voluntary movement, standing, and assisted stepping after motor complete paraplegia: a case study. The Lancet* 377, 1938-1947 (2011); Danner S M et al., *Human spinal locomotor control is based on flexibly organized burst generators. Brain: a journal of neurology* 138, 577-588 (2015); Courtine G. et al., *Transformation of nonfunctional spinal circuits into functional states after the loss of brain input. Nature neuroscience* 12, 1333-1342, (2009); Capogrosso M et al., *A brain-spine interface alleviating gait deficits after spinal cord injury in primates. Nature* 539, 284-288, (2016)).

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, the system comprising means for applying to a subject neuromodulation with adjustable stimulation parameters, said means being operatively connected with a real-time monitoring component comprising sensors continuously acquiring feedback signals from said subject. The feedback signals provide features of motion of a subject, wherein the real-time monitoring component is operatively connected with a signal processing device receiving feedback signals and operating real-time automatic control algorithms. This known system improves consistency of walking in a subject with a neuromotor impairment. A Real Time Automatic Control Algorithm is used, comprising a feedforward component employing a single input-single output model (SISO), or a multiple input-single output (MISO) model. Reference is also made to Wenger N. et al., *Closed-loop neuromodulation of spinal sensorimotor circuits controls refined locomotion after complete spinal cord injury, Science Translational Medicine*, 6, 255 (2014).

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

EP 3 184 145 A1 discloses systems for selective spatiotemporal electrical neurostimulation of the spinal cord. A signal processing device receiving signals from a subject and operating signal-processing algorithms to elaborate stimulation parameter settings is operatively connected with an Implantable Pulse Generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system advantageously allows achieving effective control of locomotor functions in a subject in need thereof by stimulating the spinal cord, in particular the dorsal roots, with spatiotemporal selectivity.

EP 2 652 676 A1 relates to a gesture control for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heartbeat, walking, etc. Similar solutions for tapping detection of a user are known from U.S. Pat. Nos. 8,326,569 and 7,742,037.

WO 2007/047852 A2 discloses systems and methods for patient interactive neural stimulation and/or chemical substance delivery. A method in accordance with one embodiment of the invention includes affecting a target neural population of the patient by providing to the patient at least one of an electromagnetic signal and a chemical substance. The method can further include detecting at least one characteristic of the patient, with the characteristic at least correlated with the patient's performance of an adjunctive therapy task that is performed in association with affecting the target neural population. The method can still further include controlling at least one parameter in accordance with which the target neural population is affected, based at least in part on the detected characteristic.

WO 2017/062508 A1 discloses a system for controlling a therapeutic device and/or environmental parameters including one or more body worn sensor devices that detect and report one or more physical, physiological, or biological parameters of a person in an environment. The sensor devices can communicate sensor data indicative of the one or more physical, physiological, or biological parameters of a person to an external hub that processes the data and communicates with the therapeutic device to provide a therapy (e.g., neuromodulation, neurostimulation, or drug delivery) as a function of the sensor data. In some embodiments, the therapeutic device can be implanted in the person. In some embodiments, the therapeutic device can be in contact with the skin of the person. The sensor devices can also communicate to the hub that communicates with one or more devices to change the environment as a function of the sensor data.

WO 2010/021977 A1 describes an orthotic apparatus for use in providing improved range of motion which allows the amount of stretch to be hydraulically powered and measured by the device but controlled by the user. Because the apparatus accurately calculates the amount of stretch, the user, together with the user's physician and therapist, can develop a rehabilitation plan based on accurate measurements. Progress is based on tangible results rather than the user's ability to tolerate pain.

EP 2 966 422 A1 describes a method for measuring parameters, such as human weight in motion. The method provides registration of signals generated by load sensors disposed in shoe insoles. Each insole has at least two load sensors, with one mounted near the heel region and the other near the toe region of foot. The specific type of motor activity is determined based on temporal correlation of the load sensor signals from both insoles and values thereof. The person's weight, including additionally carried weight, is determined by summing up load sensor signals, for a specific type of motor activity. The invention provides for the measurement of person's weight, including additionally carried weight, in real time for different types of motor activity, such as running, walking at different pace, standing.

DE 102015220741 A1 describes methods and devices for detecting dyskinetic movement disorders of a person with sensors arranged on the leg, arm and/or upper body. The sensors measure the rotation rates about a first axis parallel to the tibia, forearm and/or upper body, the rotation rates about a second axis perpendicular to the first axis and the rotation rates about a third axis or rotation rates about three axes of the leg, arm and/or upper body, some of which are non-collinear, both perpendicular to the second axis and perpendicular to the first axis. In a data processing system connected to the sensors, a value that can be assigned to a dyskinesia is calculated. Furthermore, this value is stored as a dyskinetic value, in comparison with other values as an average dyskinesis value or as a value for a dyskinetic movement disorder in comparison with at least one predetermined value.

According to the state of the art, smooth movements comparable to healthy subjects still cannot be achieved by the subject. There is a lack to have a system which overcomes the drawbacks of the prior art. In particular, there is the need of a system stimulating the patient not as a robot. A good roll of the foot and no parasitic movements are necessary during walking and smooth movements are necessary during any other movement including but not limited to cycling and/or swimming and/or rowing and/or stepping and/or sitting down and/or standing up. Thus, the goal of applying stimulation is not to control the patient as a robot, but to support the patient during training and daily life activities, including but not limited to walking and/or cycling and/or swimming and/or rowing and/or stepping and/or sitting down and/or standing up and/or or any other movement. Hence, a control system should be able to determine movement events, e.g. gait events, with criteria that are common to all kind of healthy or pathological movement, e.g. gait, and should support the patient's own natural control loop composed of the brain, nervous system, and sensory organs.

It is an object of the present invention to improve a neurostimulation system, e.g. in the field of improving recovery after neurological disorders like spinal cord injury (SCI), for example after trauma, especially in adding a control system for a movement reconstruction and/or restoration system for a patient.

This object is solved according to the present invention by a control system for a movement reconstruction and/or restoration system for a patient, with the features of claim 1. Accordingly, a control system for a movement reconstruction and/or restoration system for a patient, comprising a CNS-Stimulation Module, especially an EES-Module, configured and arranged to provide CNS-Stimulation to a patient;

and/or a PNS-Stimulation Module, especially an FES-Module, configured and arranged to provide PNS-Stimulation to a patient;

a controller configured and arranged to control the CNS-Stimulation Module and/or the PNS-Stimulation Module; and at least one sensor configured and arranged to measure at least one parameter indicative of the movement of at least one limb and/or part of a limb and/or trunk and/or the head of a patient.

The invention is based on the basic idea that in the context of neuromodulation, especially neurostimulation, the electrical stimulation parameters defining the stimulation in a movement reconstruction and/or restoration system for a patient can be controlled with said system by knowing in greater detail the position and/or current situation of at least one limb and/or at least one part of a limb such as a foot and/or a hand and/or the trunk and/or the head and/or other parts of the body of a patient. In particular, it has been found that the movement of at least one limb and/or at least one part of a limb such as a foot and/or a hand and/or the trunk and/or the head and/or other parts of the body of a patient can be used to predict more clearly the intended and/or ongoing movement and also to find out, which support the patient really needs from the system. The use of a general hardware concept including a PNS-Stimulation Module and/or a CNS-Stimulation Module, a controller, and at least one sensor configured and arranged to measure at least one parameter indicative of the movement and/or the movement speed of the head and/or trunk and/or waist and/or at least one limb and/or at least one part of a limb of a patient combined into one strategy and made available for a patient being equipped with the system enables to allow triggering the stimulation based on the movement crossing a certain threshold. Joint movements are calculated using rigorous mathematical protocols and movement abnormalities are identified by comparing a patient results to an average healthy subject. The control system may interfere with the feedback loop of the patient to enable smooth motion, e.g. a regular gait cycle, with a regular and characteristic movement of at least one limb and/or at least one part of a limb (e.g. foot) and/or another part of the body of the patient, comparable to a healthy subject. Alternatively, e.g. ground reaction forces could be measured by e.g. pressure sensors, and also other sensors could be used to measure the motion and/or position of at least one limb and/or part of a limb such as a foot and/or a hand and/or the trunk and/or the head and/or other parts of the body of a patient.

The system can be used for treatment related but not limited to restoring and or training of the movements of the patient. Such a movement could be e.g. walking, running, stepping, swimming, rowing or cycling.

By directly and/or indirectly attaching one or more sensors to at least one foot and/or another part of a leg, including but not limited to the shank and/or thigh and/or hip and/or other parts of the body including but not limited to the trunk, and/or one or two arms and/or one or two hands and/or another part of an arm and/or the head and/or the neck of the patient a precise description of the movement, e.g. angular velocity and angle during the motion, e.g. during gait cycle, can be determined to realize the reorganization of the various phases, e.g. gait phase.

The controller may be a body-worn platform that processes data that is acquired among others from the sensor and the CNS-Stimulation Module and/or the PNS-Stimulation Module to deliver the correct stimulation when a certain threshold is reached.

Neural stimulation may be achieved by electrical stimulation, optogenetics (optical neural stimulation), chemical stimulation (implantable drug pump), ultrasound stimulation, magnetic field stimulation, mechanical stimulation, etc.

Known electrical stimulation systems use either Central Nervous System (CNS) Stimulation, especially Epidural Electrical Stimulation (EES), or Peripheral Nervous System (PNS) Stimulation, especially Functional Electrical Stimulation (FES). Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso M et al., *A Computational Model for Epidural Electrical Stimulation of Spinal Sensorimotor Circuits, Journal of Neuroscience*, 33 (49), 19326-19340 (2013); Courtine G. et al., *Transformation of nonfunctional spinal circuits into functional states after the loss of brain input, Nat Neurosci.* 12(10), 1333-1342 (2009); Moraud E M et al, *Mechanisms Underlying the Neuromodulation of Spinal Circuits for Correcting Gait and Balance Deficits after Spinal Cord Injury, Neuron,* 89(4), 814-828 (2016)). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies.

PNS-Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set of reflexes (practically limited to the withdrawal reflex) or through transcutaneous stimulation the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

It is possible to provide neuromodulation and/or neurostimulation with the system to the CNS with a CNS-Stimulation Module and/or to the PNS with a PNS-Stimulation Module. Both CNS and PNS can be stimulated at the same time or also intermittently or on demand. These two complementary stimulation paradigms can be combined into one strategy and made available for a patient being equipped with the system. For example, neuromodulation and/or neurostimulation of the CNS may be used to enhance and/or restore the capabilities of the patient in terms of movement, especially in a way that the existing ways of physiological signal transfer in the patient's body are supported such that the command signals for body movement or the like still are provided by the patient's nervous system and just supported and/or enhanced or translated by the CNS-Stimulation Module. The stimulation provided by the PNS-Stimulation Module may be used to specifically steer and direct stimulation signals to specific peripheral nervous structures in order to trigger a specific movement and/or refine existing movements. Such a PNS-Stimulation may be used to refine and/or complete motion and/or the patient's capabilities of movement. It can be e.g. used to complete flexion or extension, lifting, turning or the like of inter alia but not limited to toes, fingers, arms, feet, legs or any extremities of the patient. This can be e.g. done in cases where it is realized that the neuromodulation and/or neurostimulation provided by the CNS-Stimulation Module is not sufficient to complete a movement or of the patient. Then, such a movement or intended status may be completed or supported by stimulation provided by the PNS-Stimulation Module. The PNS-Stimulation can be also used to reduce side effects or compensate for imprecisions of the CNS-Stimulation.

EES can be phasic or tonic, selective PNS-Stimulation is always phasic. Here, phasic is defined as locked to defined events in the sensing signals (decoded intention, continuous decoding, muscle activity onset, movement onset, event during defined movement (foot off or foot strike during walking for instance).

By PNS-Stimulation, a stimulation of the upper limb nerves, i.e. the radial, ulnar and/or median nerves can be provided. Also, stimulation of the lower limb nerves like the sciatic and/or femoral nerves can be provided by PNS-Stimulation. All PNS-Stimulation can be done by targeting one of the above-mentioned nerves with intra-neural electrodes (transversal or longitudinal) or epi-neural (cuff) electrodes.

By CNS-Stimulation the following nervous structures may be stimulated: for the upper limb movements the cervical spinal cord or hand/arm motor cortex may be stimulated with the CNS-Stimulation Module. For the lower limb movements, the lumbosacral spinal cord may be stimulated. All these nerves can be targeted with epidural, subdural or intra-spinal/intra-cortical stimulation.

Both PNS and CNS-Stimulation Modules may comprise implantable pulse generators (IPGs). IPGs can be used for providing the necessary stimulation current and signals for the CNS-Stimulation Module and the PNS-Stimulation Module.

The IPG produces the stimulation pulses that are delivered by a lead that may comprise a lead cable and an electrode module comprising multiple electrodes to the stimulation site, e.g. the spinal cord. For EES, the lead is positioned in the epidural space (i.e. on the outside of the dural sac, which encases the spinal cord and the cerebrospinal fluid in which the spinal cord 'floats'), on top of the spinal cord (including but not limited to the segments T12, L1, L2, L3, L4, L5, and S1 bilaterally).

It is also possible that two separated IPGs are provided, one for the PNS-Stimulation Module and one for the CNS-Stimulation Module.

The stimulation parameters for the PNS-Stimulation and the EES may be frequency, amplitude, pulse-width and the like.

Both, the CNS-Stimulation Module and PNS-Stimulation Module, as well as the combination of these stimulation modules/systems may be used in a sub-motor threshold region, i.e. an amplitude or configuration at which neuronal sensation but no motor response is evoked.

The stimulation may be performed in an open-loop manner, where a pre-defined fixed stimulation is executed without adapting to e.g. the motion of the patient. The stimulation settings may then be determined by the therapist or physiotherapist. The movement of the patient may be recorded.

The stimulation may be performed in a closed-loop manner, where feedback is used to adjust the stimulation to the movement of the patient, including but not limited to walking, running, swimming, cycling, rowing, stepping, standing up or sitting down.

The system may be also applied for a patient being supported by an external device, including but not limited to a body-weight support, a walker or crutches.

Moreover, the controller may be configured and arranged to adapt the stimulation provided by the CNS-Stimulation Module and/or the PNS-Stimulation Module on the basis of data provided by the sensor.

The controller may be used to adapt the movement phase estimation, e.g. gait phase estimation, to the specific movement, e.g. gait, of the patient. For instance, the angle and angular velocity may vary between patients, as well as for a single patient between both limbs and/or part of limbs and for different walking speeds and different assistive devices, including but not limited to a body-weight support, walker or crutches. Similarly, especially for impaired gait, not all gait events may always be present. As walking is a periodic motion, all measured signals may also be periodic. Hence, it may be possible to estimate the cadence by extracting the base frequency of the measured signals. The measured movement (or angle and/or angular velocity) may be also indicative for the current pathophysiological movement or position at the very specific moment. It can be used to correct the position and movement.

Furthermore, at least one sensor may be arranged at each limb or part of a limb and/or the head and/or the trunk of the patient.

Using one sensor for one limb or part of a limb allows to obtain limb and/or food position estimates by double integration of the measured acceleration in combination with drift correction.

For walking, said sensor may be intended to be placed on the foot to get to most information possible about the gait. The feet may be chosen as these are the lower body segments that experience the largest accelerations and angular velocities. In particular, two or more sensors placed on one foot may provide a precise description of the cadence, swing phase, stance phase, in sum including the events toe-off, midswing, heel strike, flat foot, midstance and/or heel-off can be identified. The same events and parameters can be identified for the other foot of the patient. By combining signals of both feet, together with the gait phase and cadence of the stimulation input, a reliable gait phase and cadence estimate can be provided.

The level of agreements and discrepancies between motion of the left and right foot, and the stimulation input, can be used to give an indication of the gait phase estimation reliability, e.g., the measured cadence of the left foot should be equal to the measured cadence of the right foot and the cadence of the provided stimulation, and the left foot and right foot should be (roughly) in anti-phase.

Said sensors may be lightweight and wearable, thus the sensors may not hamper the movement of the patient.

The sensor can be wirelessly connected to the other components of the system.

However, also a wired connection may be possible and used.

Moreover, the sensor may be or may comprise at least one of an inertial measurement unit (IMU), an optical sensor, a camera, a piezo element, a velocity sensor, an accelerometer, a magnet sensor, a torque sensor, a pressure sensor, a force sensor, a displacement sensor, a contact sensor, an EMG measurement unit, a goniometer, a magnetic field sensor, a hall sensor and/or a gyroscope and/or a motion tracking video camera, or a infra-red camera.

Some sensors may require fixed base station in the environment, including but not limited to magnet sensors or infra-red sensors.

Electromagnetic position sensors, optical sensors and cameras may estimate 3D position and orientation.

In particular, magnetic sensors and magnetic field sensors may be incorporated in shoes for walking on a magnetic sensor plate or inserted in the treadmill or gait phase detection device. The magnetic force may be detected and acquired by magnetic sensors under gait training.

Torque sensors may be placed on a bicycle crank for assessing the torque during cycling.

Some sensors may be worn by the patient without acquiring fixed base station, including but not limited to piezo elements, pressure sensors and/or torque sensors.

Said IMU may measure and report 3D accelerations, 3D angular velocities and 3D orientation using a combination of one or more of an accelerometer, one or more gyroscopes, and optionally one or more of a magnetometer. Optionally, a temperature sensor may also be included to compensate for the effect of temperature on sensor readings. By integrating the angular velocity assessed by said one or more gyroscopes and fusing with data from said one or more accelerometers, it may be possible to get a precise measurement of the angle of the foot. This angle may have a regular and characteristic pattern for a healthy subject but not for an injured patient. Based on these measurements the orientation of the IMU with respect to the fixed world can be estimated accurately, using standard sensor fusion algorithms.

By directly and/or indirectly attaching one or more sensors, e.g. IMUs, to the to at least one foot and/or another part of a leg, including but not limited to the shank and/or thigh and/or hip and/or other parts of the body including but not limited to the trunk, and/or at least one arm and/or one at least one hand and/or another part of an arm and/or the head and/or the neck of the patient the angular velocity and angle of at least one foot and/or another part of a leg, including but not limited to the shank and/or thigh and/or hip and/or other parts of the body including but not limited to the trunk, and/or at least one arm and/or at least one hand and/or another part of an arm and/or the head and/or the neck of the patient during motion, e.g. gait cycle, may be determined to realize the reorganization of the various motion phases, e.g. gait phase. Thanks to the angle it may be possible to compute the acceleration of the at least one foot and/or another part of a leg, including but not limited to the shank and/or thigh and/or hip and/or other parts of the body including but not limited to the trunk, and/or at least one arm and/or at least one hand and/or another part of an arm and/or the head and/or the neck of the patient in forward direction. However, also acceleration in any other direction may theoretically be determined. For example, the angle of the ankle joint varies during gait cycle with different gait events (including but not limited to toe-off, midswing, heel strike, foot flat and midstance, heel-off). This information may allow to distinguish stance and swing for a subject, e.g. an injured patient. The angle of at least one limb and/or part of a limb (including one or more joints) of a patient may be used to predict the intended and/or ongoing motion. Further, the angle of at least one limb and/or part of a limb may also be used to find out, which support the patient really needs from the control system. For open loop walking, a change in limb angle and/or part of a limb angle (including joints, e.g. ankle joint) over a certain threshold may be used to initiate a certain stimulation sequence. As just one example, the gait event heel-off may trigger the stimulation for one or more complete gait cycles. However, also other gait events, including but not limited to toe-off, midswing, heel strike, foot flat and midstance may trigger stimulation for one or more complete gait cycles. The acceleration data is sensitive to any shake during the movement, e.g. gait cycle. So, movement can be detected and therefrom also a signal derived, which is indicative for an angle, e.g. the foot angle. Similarly, single events of other periodic movements (including but not limited to running, stepping, cycling, swimming, rowing standing up or sitting down) may trigger the stimulation for one or more complete movement cycles.

For closed-loop cycling, measuring the pedal phase can simply be achieved by attaching a sensor, e.g. an IMU, to the crank of the bicycle and/or directly or indirectly to at least one foot of the patient. The pedal phase is then defined as the crank angle or the foot angle, which is directly linked to the IMU orientation. The pedal phase can be predicted given the current crank angle or foot angle and angular velocity (both directly provided by placing an IMU on a bicycle crank or at least one foot of a patient).

The sensor may be configured and arranged to be inserted and/or integrated into and/or onto an exoskeleton, tights, a belt, straps, a stretching band, a knee sock, a sock and/or a shoe of the patient.

Socks and tights may consist of or may comprise a piezoelectric textile sensor integrated in the trunk, waist, hip, knee, heel and/or toe area. An electrical response according to a mechanical stretching, pressing or pulling is delivered. In particular, socks or tights may be equipped with electrodes and/or electro conductive yarn.

The sensor may be configured and arranged to be inserted and/or arranged in the shoe and/or into the sole and/or into the insole of a shoe of the patient.

At least one shoe and/or at least one shoe sole and/or at least one shoe insole may be equipped with one or more sensors. Said one or more sensors may be placed in the heel area and/or the metatarsal area and/or the toe area. In particular, said one or more sensors may be placed either on top of the instep, at the back of the heel, and/or below the heel of the foot (e.g. in a pocket in the sole of the shoe or as an inlay sole), and/or on the sides of the foot, and/or on top of the toes. In this way, real-time and non-real-time reconstruction of foot trajectories may be done up to a few centimeters accuracy.

We define real-time as an end-to-end latency that is less than 100 ms, preferably less than 50 ms.

In particular, pressure sensors or contact sensors may be of interest in this regard for motion analysis, e.g. gait analysis. In particular, two or more pressure sensors placed on one foot may provide a precise map of the foot force. In particular, two or more sensors placed on one insole and/or sole may provide a precise description of the cadence, swing phase, stance phase, including the events toe-off, midswing, heel strike, flat foot, midstance and/or heel-off can be identified. The same events and parameters can be identified for the other foot of the patient. By combining signals of both feet, together with the gait phase and cadence of the stimulation input, a reliable gait phase and cadence estimate can be provided. For example, when a sensor is place at the heel area, lifting the foot will result in a change of pressure or the like. Also, when thinking of a piezo element in a sock or other wearable, the movement will change the applied tension on the piezo element and the sock or other wearable. Similar functionality can be used at different positions of the body of the patient.

For closed-loop cycling, measuring the pedal phase may simply be achieved by attaching a sensor, e.g. an IMU, to the crank of the bicycle or to at least one foot of the patient. The pedal phase may then be defined as the crank angle or the foot angle, which is directly linked to the IMU orientation.

The foot position, and thus the pedal position, varies during the crank cycle. For example, at low pedaling frequencies (up to 85 rpm), the heel is lowered, and the toes slightly raised when pushing, while the toes point downwards when pulling. These angles may be reflected in the position of the pedal. Therefore, the pedal phase may be predicted given the current crank angle and angular velocity (both directly provided by placing an IMU on a bicycle crank).

The control system may further comprise an electrode module, which is configured and arranged to stimulate the patient locomotor system.

Said electrodes may be implanted and have fixation elements for anchoring the electrodes in the surrounding structures at the implantation side. Motor nerves and/or sensory nerves and/or muscles may be stimulated using electrical current pulses. Given this starting point, different stimulation parameters may be identified:
- electrode configuration (which electrodes to use, polarity)
- stimulation (pulse) amplitude
- stimulation (pulse) width
- stimulation (pulse) frequency In particular, the electrode module may comprise at least one electrode, which is configured and arranged to stimulate the patient locomotor system, especially wherein the electrode is attached to and/or arranged at the limb and/or part of the limb and/or foot and/or CNS and/or spinal circuits, in particular dorsal roots.

In particular, each limb may be targeted and/or targetable with at least one electrode. Thus, each limb may be targeted by electrodes of the PNS-Stimulation Module and/or the CNS-Stimulation Module.

Stimulation of one or more limbs and/or one or more parts of a limb does not necessarily require stimulation on the locomotor system of one or more limbs and/or one or more parts of the limb, respectively, directly. As just one example, the spinal cord or the upper leg may be stimulated to induce a reflex and/or motion of the foot.

Furthermore, the at least one electrode may be configured and arranged for limb cramp stimulation to release cramp and/or detection of limb cramp.

In particular, a sensing electrode or an EMG measurement unit may sense muscle activity by means of surface or intramuscular EMG electrodes for flexors and extensors. In case of a cramp, compensatory stimulation may be delivered by the electrode(s). Stimulation patterns may vary depending on different parameters including but not limited to where the cramp is detected and/or intensity of the cramp.

If the measured movement and/or angle indicates that the foot position needs further correction, such correction may be provided directly by the electrode(s). Similar approaches may be used for other parts of the limbs.

Furthermore, the control system may comprise a pre-warning module, which is configured and arranged to provide a pre-warning signal indicative of providing an upcoming stimulation event.

Regulating the movement, e.g. gait, to a predefined reference interferes with voluntary motion of the patient. In particular, voluntary motion of the patient may have a large effect on the movement, as the patients' voluntary control may modulate the muscle activation. The movement pattern may therefore differ from comparable to a healthy subject, to impaired or reduced despite identical stimulation. The pre-warning signal may help the patient to adjust voluntary control to the respective movement planed, thus a regular movement may be performed. The pre-warning signal may include but is not limited to a sound signal, vibration, light signal, smell, taste, pain, temperature (warm, cold), humidity, draught, or the like.

In particular, the pre-warning signal may act in a sub-motor threshold region at which a sensation is evoked, but not a motor response.

There may be a communication module WSN. The communication module WSN may be a wireless network between the one or more sensors and the controller. Based on the motion feedback from the one or more sensor (s), the controller needs to be able to provide accurate gait phase and cadence estimates.

There may be a telemetry module TEL. The communication module TEL may be a wireless link between the controller and the EES Module and/or the controller and the FES Module. TEL may send data from the controller and receive by IPG. This also may include error-correction, retries, etc. The subsystem TEL may communicate commands including but not limited to or stopping the task. The telemetry module may be or may comprise a near field magnetic induction module (NFMI).

In the following it is identified which control output parameters exist and their effects on the afferent nerves, as well as their end effects on muscle activation is described. Based on this, we select which output parameters will be controlled by the control system.

BRIEF DESCRIPTION OF THE FIGURES

Further details and advantages of the present invention shall now be disclosed in connection with the drawings.

It is shown in

FIG. 3 a table specifying the fiber types, diameter, and function;

FIG. 5 a table specifying the intended movement and the involved agonist muscle and the involved antagonist muscle;

FIG. 6 functional muscle blocks (FMB) and custom muscle blocks (CMB);

DETAILED DESCRIPTION

Note that in the following we primarily refer to CNS/EES stimulation. The one skilled in the art may transfer the stimulation parameters to PNS/FES stimulation.

Figure 1:
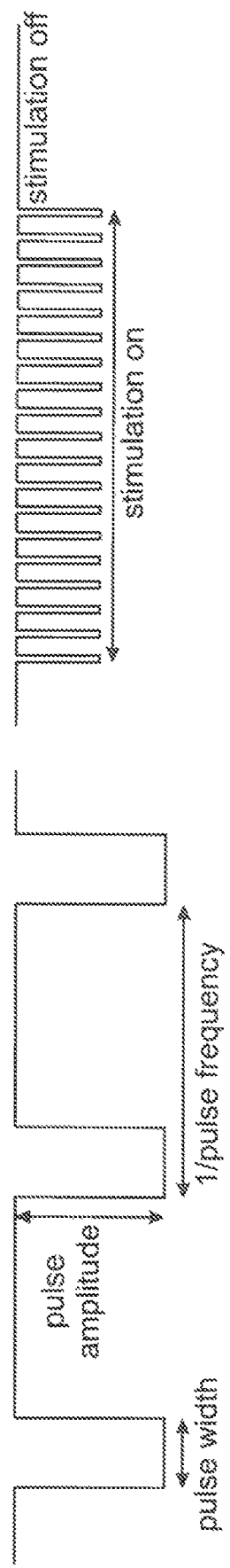
FIG. 1 a schematic, very simplified representation of a stimulation pulse delivered by a system according to the present invention.

The control system may provide stimulation data for movement reconstruction and/or restoration for stimulation of afferent nerve fibers using electrical current pulses. Given this starting point, the following stimulation parameters may be identified:

Electrode configuration (which electrodes to use, polarity)
Stimulation (Pulse) amplitude
Stimulation (Pulse) width
Stimulation (Pulse) frequency FIG. 1 illustrates a schematic, very simplified representation of the stimulation pulse, which illustrates the pulse amplitude, pulse width, and pulse frequency. Each stimulation pulse is followed by a neutralization pulse or a neutralization period (not depicted) to remove the electric charge from the tissue in order to avoid tissue damage.

The effects of each of the stimulation parameters are described below.

Electrode configuration: Stimulating a specific muscle group requires applying a specific electrical field at a specific location on the spinal cord or directly through stimulation of motorfibers (neuro-muscular stimulation), or through a limited set reflexes or by transcutaneously stimulating peripheral nerves. Therefore, in the present control system, the electrical stimulation may be delivered e.g. to the spinal cord by a lead with multiple electrodes. The location, shape, and direction of the electrical field that is produced may be changed by choosing a different electrode configuration (which electrodes are used, with which polarity and potential) that is used to deliver the current. Hence, the electrode configuration may determine to which spinal roots the stimulation is delivered, and therefore which subsequent muscles or muscle groups activity will be reinforced.

Figure 2A:
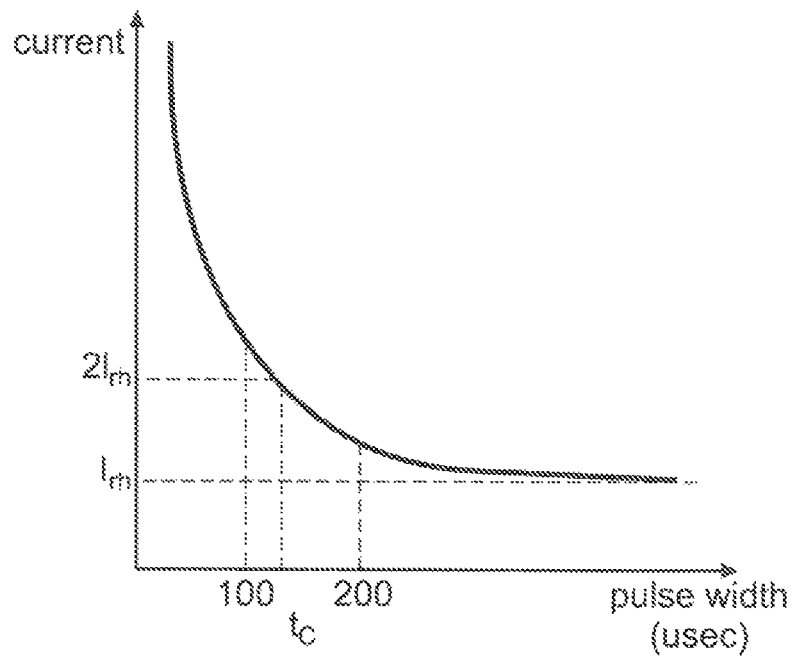
FIG. 2A, B the necessary current and necessary charge to trigger an action potential in a nerve fiber as a function of the pulse width (using a square pulse)
Figure 2B:
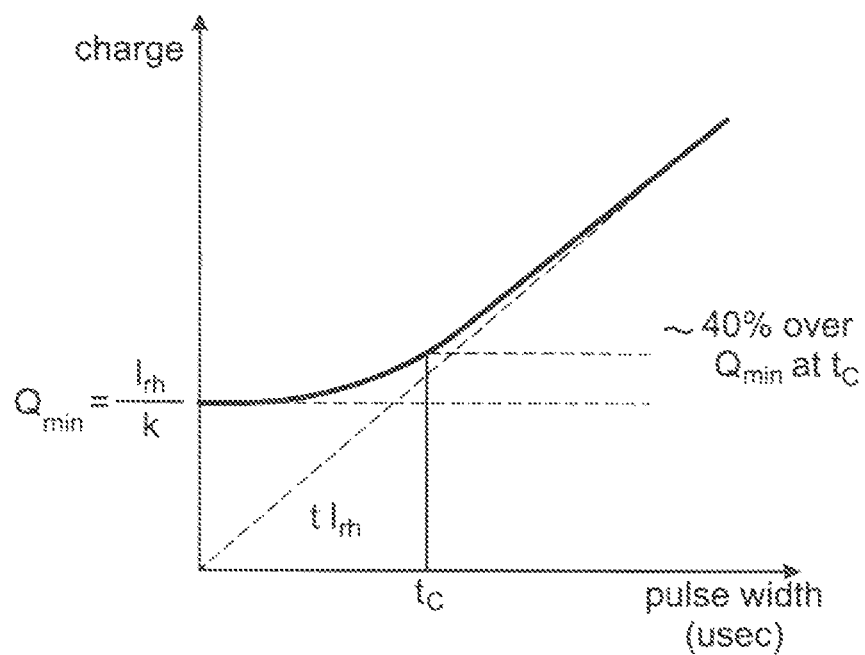

Pulse amplitude and pulse width: In FIG. 2A and FIG. 2B the necessary current and necessary charge to trigger an action potential in a nerve fiber are shown as a function of the pulse width (using a square pulse) (cf: Merrill D R. et al., *Electrical Stimulation of excitable tissue: design of efficacious and safe protocols, J Neurosci methods* 141(2):171-98 (2005)). FIG. 2A and FIG. 2B also show the rheobase current $I_{rh}$, which is the current that is required when using infinitely long pulse widths, and the chronaxie time $t_c$, which is the required pulse width at a current of $2I_{rh}$.

Although larger currents may be required at smaller pulse widths, the total required charge may decrease with decreasing pulse width, see FIG. 2B. Hence shorter pulses with higher current amplitudes may be energetically beneficial.

For smaller diameter nerves, the current-pulse width curve of FIG. 2A shifts, as smaller diameter fibers may require higher currents. Hence, a higher current may activate more nerve fibers, as also smaller diameter nerve fibers may be activated (until saturation). However, also cross-talk is increased as also more neurons from neighboring roots may be activated. Fortunately, the afferent fibers involved in motor control (fiber types Ia and Ib) may be all relatively large (12-20 μm), while the fibers involved in touch, temperature, and pain feedback (which should not be triggered) may be relatively small (0.5-12 μm), as depicted in FIG. 3. Hence, with increasing pulse width and/or current amplitude, the type Ia and Ib fibers may be the first to be recruited. This may enable recruiting (most of) the relevant fibers while keeping cross-talk and patient discomfort to a minimum.

Pulse frequency: The pulse frequency may determine the frequency of the action potentials generated in the afferent nerves, assuming sufficient charge is delivered each pulse to trigger the action potentials. As no new action potential can occur in a nerve during the refractory period, the frequency of the triggered action potentials will saturate at high pulse frequencies. This saturation point is generally at around 200 Hz for afferent fibers (Miller J P. et al., *Parameters of Spinal Cord Stimulation and Their Role in Electrical Charge Delivery: A Review. Neuromodulation: Technology at the Neural Interface* 19, 373-384, (2016)). However, stimulation at frequencies above the saturation point may still be beneficial, as by increasing frequency the total charge delivered per unit time (i.e. charge per second) can be increased without changing current amplitude or pulse width (Miller J P. et al., *Parameters of Spinal Cord Stimulation and Their Role in Electrical Charge Delivery: A Review. Neuromodulation: Technology at the Neural Interface* 19, 373-384, (2016)).

Pulse positioning: Many tasks, including walking, require simultaneous activation of multiple muscle groups. Hence, to support these tasks, multiple muscle groups may need to be stimulated simultaneously, each requiring a specific electrical field and pulse frequency. When applied simultaneously, these different electrical fields may interact with each other, potentially leading to unintended and uncontrolled effects. Therefore, to avoid this situation, care should be taken that the individual stimulation pulses and their neutralization periods targeting different muscle groups are not applied simultaneously. This may not be considered a stimulation parameter but does identify a required system feature: a pulse positioning algorithm.

The previous section describes the effect of the stimulation parameters on triggering action potentials in afferent nerve fibers. Although triggering these action potentials is an essential step in the therapy, in the end the stimulation should enable or support the patient in performing specific lower body motions, which may require the activation of specific muscles or muscle groups. The effect of the triggered action potentials in afferent nerve fibers on muscle activation may be filtered inside the spinal cord through spinal reflex circuits and modulated through the voluntary control of the patient. Hence, the effect of the stimulation parameters on muscle activation may be not perfectly clear and may be affected by intra- and inter-Patient variations. The following aspects may be of relevance here:

Different patients may have different levels of voluntary control over their lower body, depending on the type and severity of their SCI lesion level and state of (spontaneous) recovery.

Stimulation of afferent nerve fibers may assist or enable activation of the corresponding muscles but may not necessarily enforce motion. The patient may modulate the activation (e.g. make a large or small step without changing the stimulation), or even resist motion of the leg completely. This may vary per patient and may change with increasing recovery.

Conjecture: Because the spinal cord floats in the cerebrospinal fluid, the distance between the spinal cord and the Lead electrodes may vary (mostly as a function of the Patient's posture: prone—large distance, supine—small distance). Another hypothesis may be that due to posture changes, the layer thickness of low conductive epidural fat between the Lead electrodes and the dura/cerebrospinal fluid a changing, leading to an impedance change as seen by the electrodes, and resulting in an altered current/voltage delivered stimulation by the electronics. As a result, the effect of the applied stimulation (including muscle onset and saturation) may also vary with the patient's posture. Although this conjecture is not proven, patients may successfully make use of the described effects to modulate the stimulation intensity by varying their posture: bending forward reduces the intensity, bending backward increases it.

Pulse frequencies between 40 and 120 Hz may mostly being used, although it may theoretically be possible to stimulate up to 500 Hz as this may have benefits for selectivity in muscle activation and improved voluntary control of the patient.

It may be possible that generally increasing the pulse amplitude may not lead to increased recruitment of muscle fibers (with corresponding increased cross-talk), and that increasing the stimulation frequency may lead to increased muscle activation without affecting cross-talk. However, increasing the stimulation frequency may reduce the intensity of natural proprioception and result in a decreased feeling in the leg of the patient. This is probably due to the collision of natural sensory inputs with antidromic action potentials generated by the electrical stimulation. At high frequency (above 100 Hz), patients may even report a complete loss of sensation of the leg and "feel like walking with their legs being absent". This is a non-comfortable situation requiring the patient to make a leap of faith at each single step, believing that the leg that he/she does not feel anymore will support him/her during the next stance phase.

Adjusting the balance between stimulation amplitude and frequency may therefore be necessary to find the optimal compromise between cross-talk limitation and loss of sensation. Simulations suggest that a possible workaround may be to shift the stimulation domain to lower amplitudes and even higher frequency, such that with a minimal number of stimulated fibers the same amount of activity is triggered in the spinal cord. Such hypothesis requires validation via additional clinical data. Finally, it may also be identified that different patients require different stimulation, i.e. that the optimal frequency and amplitude settings can may vary highly between patients. Hence, the relation between stimulation amplitude and frequency on muscle activation may be still for a large part unclear. Moreover, the optimal stimulation settings may vary during the day, the assistive device that is used (crutches, walker, etc.), over time with improved recovery, and with the goal of the training or activity.

Timing: Apart from applying the correct electrical field at the right location on the spinal cord, they also may need to be applied at the correct moments in time and correctly sequenced. The relevant timing aspects that are identified are listed below.

Figure 4:
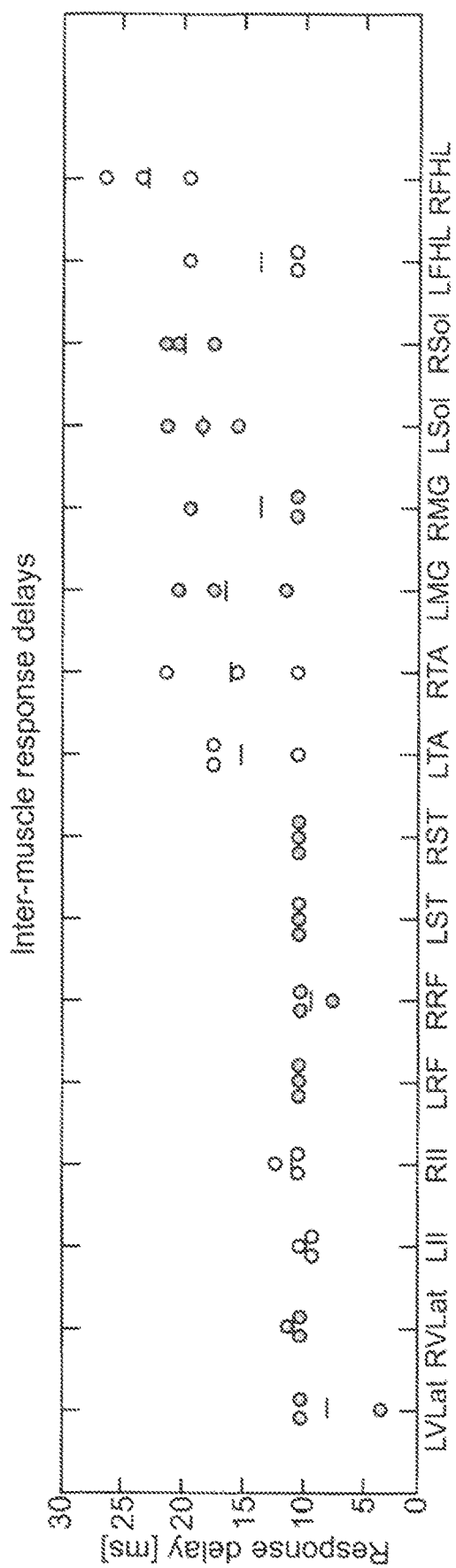
FIG. 4 the relationship between response delay and inter-muscle response delays.

There is a delay from stimulation on the spinal cord to muscle activation (typical values in the order of 0-30 ms depending on the muscle, see FIG. 4, LVLat=left vastus lateralis, RVLat=right vastus lateralis, Lll=left iliopsoas, Rll=right iliopsoas, LRF=left rectus femoris, RRF=right rectus femoris, LST=left semitendinosus, RST=right semidentinosus, LTA=left tibialis anterior, RTA=right tibialis anterior, LMG=left medial gastrocnemius, RMG=right medial gastrocnemius, LSol=left soleus, RSol=right soleus, LFHL=left flexor halluces longus, RFHL=right flexor halluces longus).

While EES enables patients to perform motions, the patient may need to be able to predict when the stimulation will occur in order to make the best use of the stimulation. Likewise, suppressing motion while stimulation is provided also requires that the patient knows when to expect the stimulation. Hence, predictability of the stimulation timing is essential.

When the stimulation is not synchronized to the patient's (intended) motion, the patient may not be able to perform a proper movement. Here, this may mean that the stimulation needs to be predictable by the patient, as the patient needs to synchronize to the stimulation.

The duration of the stimulation for leg swing during walking may need to be finely tuned. For some patients, increasing the duration of this stimulation by 100 ms made the patient jump instead of performing a proper step.

20 ms may be a sufficient resolution for tuning the stimulation timings (i.e. the on/off times of the stimulation for a specific muscle group may not need to be controlled at a precision below 20 ms). Given current data availability, controlling the timings at resolutions below 20 ms may not seem to improve the effectiveness of the stimulation.

Based on the previous sections, the stimulation parameters may be selected to control in the control system. This may determine the control output space that is used, and therefore the complexity of the control problem and the potential effectiveness of the control system.

First it is discussed which parameter spaces can be reduced or eliminated. The remaining control output space is summarized below.

Electrode configuration: Walking, as well as other movements of the lower extremities, may be composed of well-coordinated flexion and extension of lower body joints by contraction of agonist muscles and relaxation of antagonist muscles. The specific set of agonist and antagonist muscles for joint specific flexion and extension may be grouped, and as the number of joints is limited, this means that only a small discrete set of muscle groups may be needed to be stimulated. For each joint flexion and extension, the Space Time Programmer (STP, for e.g. programming space and time of the stimulation) will support creating the optimal electrode configuration for activation of the agonist muscles while avoiding activation of the antagonist muscles (as well as avoiding activation of muscles on the contralateral side). This may be done in a procedure called the functional mapping. We define the Functional Muscle Blocks (FMB), as the resulting stimulation configurations for each specific muscle group. At least 12 specific FMBs have been identified for using the control system, these are listed in FIG. 5 with their corresponding agonists and antagonists.

As knee flexion and hip extension both involve the semitendinosus, it is physically not possible to target knee flexion and hip extension separately. Therefore, FIG. 5 does not include Knee Flexion (this could be considered redundant to Hip Extension).

Next to the 12 FMB listed in FIG. 5, it is also envisioned that the trainer/therapist/physiotherapist may create Custom Muscle Blocks (CMB). Creating CMB may be useful in case the trainer/therapist/physiotherapist wants to apply stimulation that does not specifically target any of the 12 muscle groups targeted by the FMB, or in case the trainer/therapist/physiotherapist wants to use a variant of one of the 12 FMB in a specific task.

Hence, by limiting the electrode configurations to the discrete set of FMB and CMB (versus an infinite number of possible electrode configurations), the control problem complexity may be reduced considerably without significantly affecting the potential effectiveness of the control system. Stimulation for a task is then reduced to stimulation of (a subset of) the predefined FMB and CMB, see FIG. 6. For this example, the Right Trunk Stability is used in both Task 1 and Task 2.

The functional mapping procedure may require measuring the response of each of the muscles listed in FIG. 5 with EMG sensors. Due to the large number of muscles, this requires attaching many EMG sensors to the patient (which is time consuming) and processing a large amount of data. Moreover, as motion of the patient may induce signal artifacts, the functional mapping may be best performed while the patient is not moving. For these reasons, the functional mapping procedure may be performed in a separate session using the space time programmer, e.g. for programming of space and time of stimulation, and not e.g. adaptively within the control system. Hence, the configuration of FMB and CMB may be considered as a given to the control system.

Pulse width: From the viewpoint of triggering action potentials in afferent nerve fibers, the parameters pulse width and pulse amplitude may be tightly linked and may together determine which afferent nerve fibers are recruited. Increasing the pulse width may allow to reduce the amplitudes and decreasing the pulse width may allow reducing energy consumption (as the total required charge for triggering an action potential decreases with decreasing pulse width, see FIG. 2B and stimulating more FMB simultaneously or at higher frequencies. However, from a control perspective the two parameters may be (almost) redundant, as increasing either parameter may lead to the recruitment of more afferent nerve fibers over a larger area.

Pulse widths below chronaxie time $t_c$ may quickly require high currents (and thus high voltages), which is difficult to produce and may lead to patient discomfort. Beyond $t_c$, the strength-duration curve of FIG. 2A is almost flat, so increasing pulse width beyond $t_c$ has little effect on the required amplitudes while it increases total power consumption. Also considering that having a fixed pulse width simplifies the pulse positioning, the pulse width is chosen to be fixed (at a value near chronaxie time $t_c$ such that both energy consumption and required current amplitudes remain low, where $t_c \approx 200$ µs for afferent dorsal root nerve fibers in humans). This reduces the complexity of the control problem by reducing the number of output parameters.

This may leave the following stimulation parameters to be controlled over time by the control system:
Which FMBs to stimulate
Stimulation amplitude per FMB
Stimulation frequency per FMB The pulse positioning may be considered a lower level problem and may therefore be not a direct output of the control system (system feature). The pulse positioning may be performed by the IPG.

Although combining amplitude and frequency to a single 'intensity' parameter has been considered, doing so may not be envisioned for the control system, as these parameters may have very different effects. On triggering action potentials in afferent nerve fibers, the amplitude and frequency may be independent parameters: the amplitude determines in which afferent nerve fibers action potentials are triggered, the frequency determines the rate at which they are triggered. Hence, in principle the amplitude determines which muscle fibers are activated, the frequency determines how hard, although it is unclear if the independence of the two parameters also holds for muscle activation due to the signal processing that occurs in the spinal cord. Moreover, it may be apparent that for some patients changing the amplitude gives the best results, while for other patients the frequency may be the more useful parameter.

As we do not know the precise relation between frequency and amplitude in the clinical context it cannot be recommended to combine frequency and amplitude to single parameter, until more data is available. Hence, the stimulation frequency and amplitude will be controlled independently from each other.

In the following the stimulation system (e.g. IPG), the controller and the sensor of the present invention are described in greater detail.

Stimulation system, here IPG: Implantable Pulse Generator. A battery powered device that generates the electrical stimulation, subcutaneously implanted. Its intended use is to deliver electrical stimulation to the Lead based on command received from the controller.

Controller: Battery powered, body worn device (directly or indirectly), receiving data from sensor(s) and able to send stimulation commands to the IPG for specific tasks (i.e. an activity/training exercise). Its intended use is to determine optimal stimulation settings for any given task and providing this information to the IPG. In addition, this device can take the IPG out of shelf mode, charge the IPG battery transcutaneous, and initiate an IPG-Lead integrity test.

Sensors: Battery powered, body worn sensors (directly or indirectly), collecting motion data, and sending it to the controller. Its intended use is to capture body motion parameters.

The control system may further comprise a programmer: The programmer, or also called the clinician programmer, can be used to receive inter alia stimulation parameter, patient data, physiological data, training data etc.

It may comprise a Space Time Programmer (STP) for e.g. programming space and time of the stimulation, a Physiotherapist Programmer (PTP) for e.g. allowing the physiotherapist adjustment to the stimulation, and a Patient Programmer (PP) for e.g. allowing the patient to select a specific stimulation program.

The Space Time Programmer (STP), Physiotherapist Programmer (PTP), and Patient Programmer (PP) can be embodied as applications installed on a mobile device that communicate with the controller. They are used by the treating physician (TP), a physiotherapist (PT), or the Patient to provide inputs to the controller, e.g., selecting, starting, and stopping a task or configuring stimulation parameters.

The Programmer can allow adjusting the stimulation parameters of a task, while the task is running. This enables the user to tune the stimulation without having to start and stop the task, which would be very cumbersome at the start of the rehabilitation training, when all stimulation partitures are developed and tuned.

Generally speaking, the programmer may have the following structure:

In a first embodiment, the programmer can be embodied such that it is possible to receive inter alia but not limited to stimulation parameters, patient data and the like, check and/or reprogram the stimulation data and send it back to e.g. the controller.

The programmer is in this first embodiment capable to receive data from the implanted (part of the) system (e.g. the controller), display data, receive input from the user and then send it back to the controller. In other words: The programmer can receive, process and re-send the data.

In a second embodiment, the programmer may receive data from a remote database. The database may be e.g. linked with the stimulation system via a separate interface, which is configured for data transfer from the system to the database only.

The programmer is in this second embodiment capable to receive data from the remote database, display data, receive input from the user and then send it to the controller. In other words: The programmer is only in connection with the controller for sending data, it does not receive data from the controller or any implanted system parts.

Figure 7:
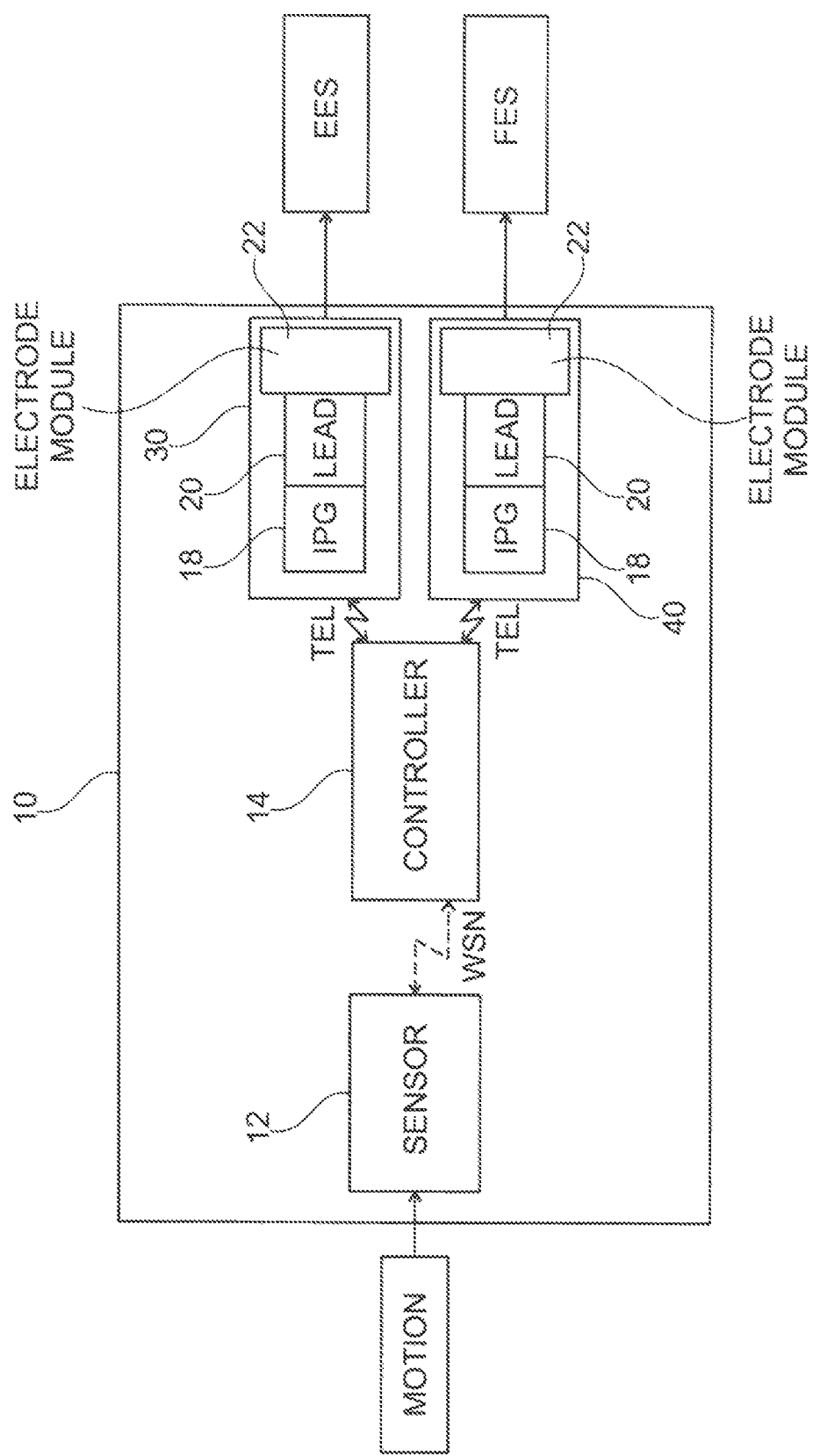
FIG. 7 a general layout of an embodiment of the control system for a movement reconstruction and/or restoration system for a patient P according to the present invention.

FIG. 7 shows a general layout of an embodiment of the control system 10 for a movement reconstruction and/or restoration system for a patient P according to the present invention.

The control system 10 comprises at least one sensor 12.

Furthermore, the control system 10 comprises in the shown embodiment a controller 14.

Additionally, the control system 10 comprises a CNS-Stimulation Module 30 for CNS-Stimulation.

In this embodiment, the CNS-Stimulation Module 30 is a EES-Module 30 for EES.

The EES-Module 30 comprises an implantable pulse generator (IPG) 18.

The EES-Module further comprises a lead 20.

The lead 20 comprises a lead cable.

The lead 20 further comprises an electrode module 22.

The electrode module 22 comprises one or more electrodes.

Additionally, the control system 10 comprises a PNS-Stimulation Module 40 for PNS-Stimulation.

In this embodiment, the PNS-Stimulation Module 40 is a FES-Module 40 for FES.

The FES-Module 40 comprises an IPG 18.

The FES-Module 40 further comprises a lead 20.

The lead 20 comprises a lead cable.

The lead 20 further comprises an electrode module 22.

The electrode module 22 is configured and arranged to stimulate the locomotor system of the patient.

The electrode module 22 comprises one or more electrodes.

The one or more sensors 12 is/are connected to the controller 14.

The connection between the one or more sensors 12 and the controller 14 is in the shown embodiment a direct connection.

However, also an indirect connection (i.e. with another component of the control system 10 in between) would be generally possible.

The connection between the one or sensors 12 and the controller 14 is established in the shown embodiment via a wireless network WSN.

However, also a cable-bound connection would be generally possible.

The controller 14 is connected to the IPGs 18 in the shown embodiment via a direct connection.

However, also an indirect connection (i.e. with another component of the control system 10 in between) would be generally possible.

The connection between the controller 14 and the IPG 18 of the EES-Module 30 is established in the shown embodiment via a wireless link TEL.

The connection between the controller 14 and the IPG 18 of the FES-Module 40 is established in the shown embodiment via a wireless link TEL.

However, also a cable-bound connection would be generally possible.

The IPG 18 of the EES-Module 30 is connected to the lead 20 of the EES-Module 30 via a direct connection.

The IPG 18 of the FES-Module 40 is connected to the lead 20 of the FES-Module 40 via a direct connection.

However, also an indirect connection could be possible.

In one embodiment, the controller 14 is body-worn, the IPG 18 is implanted in the body, and the one or more sensors 12 is/are directly attached to at least one of the patient's limbs or to a training entity, e.g. a bicycle crank.

However, also an indirect attachment could be generally possible.

By means of the one or more sensors 12 signals indicative for a motion, e.g. movement of a limb, e.g. an arm or leg, or a foot or hand, can be sensed and used by the control system 10.

The sensor signals are transferred to the controller 14 and there processed.

The controller 14 processes data that is from e.g. the sensor 12 and the IPG 18.

By means of the controller 14 the control software is executed.

The controller 14 controls the CNS-Stimulation Module 30, i.e. the EES-Module 30.

The controller 14 controls the PNS-Stimulation Module 40, i.e. the FES-Module 40.

In this embodiment, the controller 14 adapts the stimulation provided by the CNS-Stimulation Module 30 and/or the PNS-Stimulation Module 40 on the basis provided by the sensor 12

The controller 14 programs the IPG 18 to deliver the correct stimulation via the lead 20 and the electrode module 22.

In this embodiment, the controller 14 programs the IPG 18 of the EES-Module 30 to deliver EES via the lead 20 and the electrode module 22.

In general, the electrodes of the electrode module 22 are configured and arranged to stimulate the patient locomotor system, especially wherein the at least one electrode is attached to and/or arranged at a limb and/or part of a limb and/or a foot and/or the CNS and/or spinal circuits, in particular dorsal roots.

For EES, here the lead 20 is positioned in the epidural space (i.e. on the outside of the dural sac, which encases the spinal cord and the cerebrospinal fluid in which the spinal cord 'floats'), on top of the spinal cord (including but not limited to the segments T12, L1, L2, L3, L4, L5, and S1 bilaterally).

In this embodiment, the controller 14 programs the IPG 18 of the FES-Module 40 to deliver FES via the lead 20 and the electrode module 22.

In this embodiment, FES is provided directly through stimulation of motorfibers (neuro-muscular stimulation).

Alternatively, FES could be provided by or through a limited set of reflexes (practically limited to the withdrawal reflex) or by transcutaneous stimulation of the peripheral nerves.

It is also possible that the control system 10 comprises only one IPG 18 for both EES and FES.

In other words, it is also possible that the control system 10 comprises only one IPG 18 which is shared by the EES-Module 30 and the FES-Module 40.

It is also possible that the control system 10 comprises only one IPG 18, in particular only for EES.

It is also possible that the control system 10 comprises only one IPG 18, in particular only for FES.

Alternatively, also other suitable stimulation signals may be provided.

Not shown in FIG. 7 is that the at least one sensor 12 is an inertial measurement unit (IMU).

Said IMU comprises an accelerometer, a gyroscope, and a magnetometer.

Said IMU measures and reports 3D accelerations, 3D angular velocities and 3D orientation using a combination of an accelerometer and a gyroscope.

In an alternative embodiment, an IMU could use a combination of one or more of an accelerometer, one or more gyroscopes, and optionally one or more of a magnetometer.

By integrating the angular velocity assessed by the gyroscope and fusing with data from the accelerometers, a precise measurement of the angle of the foot is obtained. Based on these measurements the orientation of the IMU 12 with respect to the fixed world is estimated accurately, using standard sensor fusion algorithms.

So, movement is detected and therefrom also a signal derived, which is indicative for an angle, e.g. the foot angle.

Real-time and non-real-time reconstruction of foot trajectories may be done up to a few centimeters accuracy.

In this embodiment, real-time is defined as an end-to-end latency that is less than 100 ms, preferably less than 50 ms.

In an alternative embodiment, the at least one sensor 12 could also be one of an optical sensor, a camera, a piezo element, a velocity sensor, an accelerometer, a magnetic sensor, a torque sensor, a pressure sensor, a displacement sensor, an EMG measurement unit, a goniometer, a hall sensor, a gyroscope and/or a motion tracking video camera, or a infra-red camera.

Some sensors 12 could require fixed base station in the environment, including but not limited to magnet sensors or infra-red sensors.

Electromagnetic position sensors, optical sensors and cameras could estimate 3D position and orientation.

Torque sensors could be placed on a bicycle crank for assessing the torque during cycling.

Some sensors 12 could be worn by the patient without acquiring fixed base station, including but not limited to piezo elements, pressure sensors and/or torque sensors.

By directly and/or indirectly attaching one or more sensors 12, e.g. IMUs 12, to the trunk and/or waist and/or head and/or neck and/or at least one limb and/or one or more parts of a limb, including one or more joints, the angular velocity and angle of the trunk and/or head and/or neck and/or at least one limb and/or one or more parts of a limb during motion, e.g. gait cycle could be determined to realize the reorganization of the various motion phases, e.g. gait phase.

Thanks to the angle it could be possible to compute the acceleration of the limb and/or part of the limb in the forward direction.

However, also acceleration in any other direction may theoretically be determined.

In particular, the angle of the ankle joint varies during gait cycle with different gait events (including but not limited to toe-off, midswing, heel strike, foot flat and midstance, heel-off).

The angular velocity and angle of the trunk and/or head and/or neck and/or at least one limb and/or one or more parts of a limb of a patient P could be used to predict the intended and/or ongoing motion.

The angle of at least one limb and/or part of a limb can also be used to find out which support the patient really needs from the control system 10.

For open loop walking, e.g. a change in limb angle and/or part of a limb angle (including joints, e.g. ankle joint) over a certain threshold could be used to initiate a certain stimulation sequence.

In particular, the gait event heel-off could trigger the stimulation for one or more complete gait cycles.

However, also other gait events, including but not limited to toe-off, midswing, heel strike, foot flat and midstance could trigger stimulation for one or more complete gait cycles.

Note that also single events of other periodic movements could trigger the stimulation for one or more complete motion cycles.

In other words, the control system 10 is not only applicable for walking/gait cycle, but also for other movements, including but not limited to cycling, swimming, stepping, rowing, sitting down, standing up, squatting, etc.

Figure 8A:
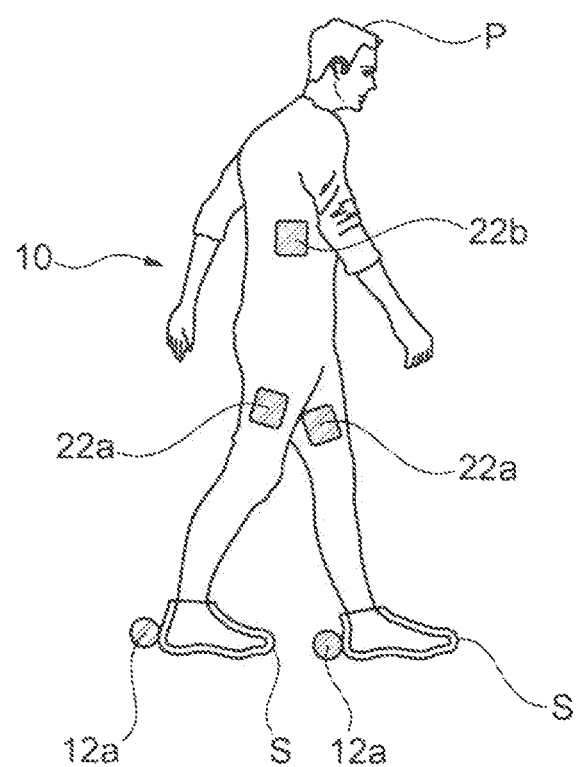
FIG. 8A a perspective view of a patient equipped with the control system disclosed in FIG. 7 comprising two sensors according to the present invention.
Figure 8B:
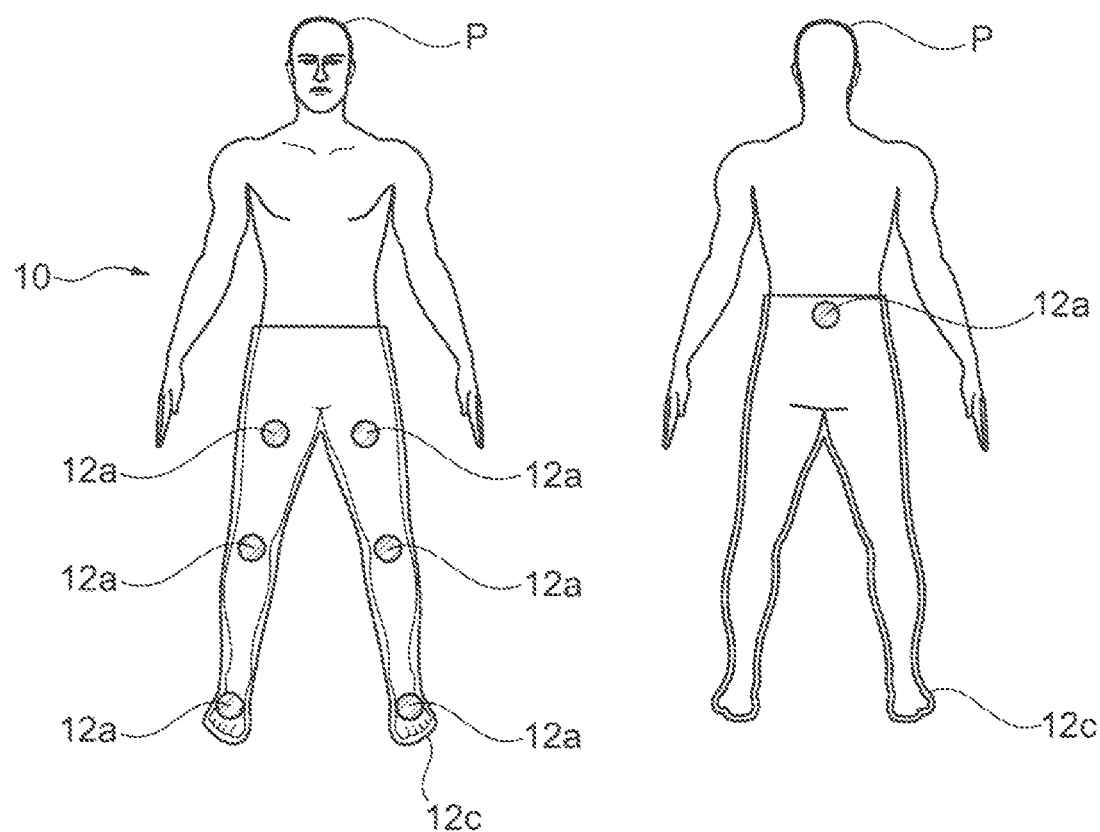
FIG. 8B a perspective view of a patient equipped with the control system disclosed in FIG. 7 comprising seven sensors.

Two or more sensors 12 could form a sensor network, cf. also FIG. 8B.

In an alternative embodiment, the control system 10 could be connected to a training entity via a wireless link.

Not shown in FIG. 7 is the fact that the one or more sensors 12 could be connected to, inserted and/or integrated in a training entity, included but not limited to an exoskeleton, a body weight support, a treadmill and/or crutches.

Not shown in FIG. 7 is that for closed-loop cycling, measuring the pedal phase can simply be achieved by attaching a sensor, e.g. an IMU, to the crank of the bicycle or to the food (or both feed) of the patient.

The foot position, and thus the pedal position, varies during the crank cycle.

For example, at low pedaling frequencies (up to 85 rpm), the heel is lowered, and the toes slightly raised when pushing, while the toes point downwards when pulling.

These angles could be reflected in the position of the pedal.

The pedal phase could then be defined as the crank angle, which is directly linked to the IMU orientation.

Note that the pedal phase could also be predicted given the current crank angle and angular velocity (both directly provided by placing an IMU on a bicycle crank).

For closed-loop cycling, the stimulation partiture defines spatial stimulation, at which pedal phase, amplitudes, and frequencies.

In an alternative embodiment the training entity could also be the patient himself or herself.

It is possible that the controller 14 tracks and/or estimates a training entity movement for translating it into stimulation data, based on the estimated movement, being provided by the IPG 18 to the patient for the patient training.

Not shown in FIG. 7 is that the control system 10 could comprise a pre-warning module, which is configured and arranged to provide a pre-warning signal indicative of providing an upcoming stimulation event.

In particular, the pre-warning signal may act in a sub-motor threshold region at which a sensation is evoked, but not a motor response.

It is also not shown in FIG. 7 that a pulse generator could generally also be a non-implantable pulse generator.

It is also not shown in FIG. 7 that remote control of the control system 10 could be generally possible.

It is also not shown in FIG. 7 that the control system 10 could further comprise or could be linked to a programmer.

The programmer could be used to receive inter alia stimulation parameter, patient data, physiological data, training data etc.

The programmer could comprise a Space Time Programmer (STP) for e.g. programming space and time of the stimulation, a Physiotherapist Programmer (PTP) for e.g. allowing the physiotherapist adjustment to the stimulation, and a Patient Programmer (PP) for e.g. allowing the patient to select a specific stimulation program.

The Space Time Programmer (STP), Physiotherapist Programmer (PTP), and Patient Programmer (PP) could be embodied as applications installed on a mobile device that communicate with the controller.

They could be used by the treating physician (TP), a physiotherapist (PT), or the Patient to provide inputs to the controller, e.g., selecting, starting, and stopping a task or configuring stimulation parameters.

The programmer could allow adjusting the stimulation parameters of a task, while the task is running.

This enables the user to tune the stimulation without having to start and stop the task, which would be very cumbersome at the start of the rehabilitation training, when all stimulation partitures are developed and tuned.

Generally speaking, the programmer could have the following structure:

In one embodiment, the programmer could be embodied such that it is possible to receive inter alia but not limited to stimulation parameters, patient data and the like, check and/or reprogram the stimulation data and send it back to e.g. the controller.

The programmer could in this first embodiment be capable to receive data from the implanted (part of the) system (e.g. the controller), display data, receive input from the user and then send it back to the controller.

In other words: the programmer could receive, process and re-send the data.

In another embodiment, the programmer could receive data from a remote database.

The database could be e.g. linked with the stimulation system via a separate interface, which could be configured for data transfer from the system to the database only.

The programmer in this second embodiment could be capable to receive data from the remote database, display data, receive input from the user and then send it to the controller.

In other words: the programmer could be only in connection with the controller for sending data, it could does not receive data from the controller or any implanted system parts.

FIG. 8A shows a perspective view of a patient P equipped with the control system disclosed in FIG. 7 comprising two sensors according to the present invention.

In this embodiment, a patient P is equipped with said control system 10 disclosed in FIG. 7 comprising two sensors 12, which are here two IMUs 12a attached to the shoes S of the patient P.

In particular, one IMU 12a is attached to the left shoe S of the patient P and one IMU 12a is attached to the right shoe S of the patient P.

In this embodiment, the IMUs 12a are placed on the heel area of the shoes S of the patient P.

In this embodiment, the control system 10 comprises also two electrodes 22a for FES.

In particular, one electrode 22a for FES is attached to the left leg of the patient P and one electrode 22a for FES is attached to the right leg of the patient P.

However, it could be generally possible that each leg of the patient P is equipped with two or more electrodes 22a for FES.

In particular, one electrode 22a for FES is attached to the left upper leg of the patient P and one electrode 22a for FES is attached to the right upper leg of the patient P.

However, it could be generally possible that the one or more electrodes 22a for FES are placed at any other position (s) of the legs of the patient P.

Further, in this embodiment, the control system 10 comprises one electrode 22b for EES.

The electrode 22b for EES is attached to the dorsal roots of the patient P.

However, also positioning two or more electrodes 22b for EES to the dorsal roots, in the epidural space, or on top of the spinal cord could be generally possible.

In general, each limb could be targeted and/or targetable with at least one electrode 22a and/or 22b.

In other words, each limb could be targeted by one or more electrodes 22b for EES and/or one or more electrodes 22a for FES.

According to FIG. 7, by means of the two IMUs 12a attached to each shoe S of the patient P each movement of the left foot and right foot of the patient P is sensed and used by the control system 10.

The controller 14 tracks and/or estimates the movement of the foot of the patient P for translating it into stimulation data, based on the estimated movement, being provided by the IPG 18 to the patient P.

The IPG 18 provides FES via the lead 20 and the electrode module 22 with the one or more electrodes 22a.

The IPG 18 provides EES via the lead 20 and the electrode module 22 with the one or more electrodes 22b.

In an alternative embodiment, one sensor 12 may be arranged at each limb of a patient.

In an alternative embodiment, the IMUs 12a could be placed at and/or inserted in, and/or in different positions in the shoe S or in the shoe sole and/or in the shoe insole.

In an alternative embodiment, the control system 10 could comprise only one IMU 12a positioned directly or indirectly to the left foot or the right foot, or the left shoe S or the right shoe S of the patient P.

Alternatively, a patient equipped with the control system 10 disclosed in FIG. 7 could be equipped with two or more sensors 12 for at least one limb, cf. also FIG. 8B.

In particular, at least one sensor 12 could be inserted and/or arranged in the shoe S and/or into the sole and/or into the insole 100 of a shoe S of a patient.

Said sensors 12 may be positioned at any place from the distal end to the proximal end of the foot, in particular in the heel area and/or the metatarsal area and/or the toe area, and/or the sides of the feet.

In an alternative embodiment, the one or more sensor(s) 12 could be inserted and/or integrated into and/or onto an exoskeleton, tights, a belt, straps, a stretching band, a knee sock, a sock and/or a shoe S of the patient.

However, in general it could also be possible that socks and/or tights consist of and/or comprise a piezoelectric textile sensor integrated in the trunk, waist, hip, knee, heel, toe area.

An electrical response according to a mechanical stretching, pressing or pulling could be delivered.

In particular, socks and/or tights could be equipped with electrodes and/or electro conductive yarn.

Alternatively, magnetic sensors and magnetic field sensors could be incorporated in shoes S for walking on a magnetic sensor plate or inserted in the treadmill or gait phase detection device.

The magnetic force could be detected and acquired by magnetic sensors under gait training.

Not shown in FIG. 8A is that for assessing upper body motion and/or arm motion and/or hand motion, the one or more sensors 12 could be inserted and/or integrated into and/or onto clothing or the like for the upper body and/or arms, and or hands, including but not limited to a top, a longsleeve, a pullover, a jacket, one or more arm sleeves, gloves, and/or one or more armlets.

Not shown in FIG. 8A is that the electrodes 22a/22b could also be configured and arranged for limb cramp stimulation to release cramp and/or detection of limb cramp.

Not shown in FIG. 8A is that stimulating motion of one or more limbs and/or one or more parts of a limb does not necessarily require stimulating on the locomotor system of one or more limbs and/or one or more parts of the limb, respectively, directly.

As just one example, the spinal cord or the upper leg may be stimulated to induce a reflex and/or motion of the foot.

FIG. 8B shows a perspective view of a patient equipped with the control system disclosed in FIG. 7 comprising seven sensors.

In this embodiment, a patient P is equipped with said control system 10 disclosed in FIG. 7 comprising seven sensors 12, which are here seven IMUs 12a.

The seven IMUs 12a build a sensor network 12c.

In this embodiment, the seven IMUs 12a are attached to the lower body of the patient P.

In particular, one IMU 12a is placed centrally in the hip area, whereas the left leg is equipped with three IMUs 12a placed on the foot, the lower leg, and the upper leg, and whereas the right leg is equipped with three IMUs 12a, placed on the foot, the lower leg, and the upper leg, respectively.

However, also alternative placements of a different number of IMUs 12a along the legs and/or feet and/or the lower body could be generally possible.

According to FIG. 7, by means of the seven IMUs 12a placed on the lower body of the patient P each movement of the legs and feet of the patient P is sensed and used by the control system 10.

According to FIG. 8B, both FES and EES can be provided by the IPG 18, the lead 20 and the electrode module 22 with respective electrodes 22a and 22b.

Not shown in FIG. 8B is that any part of the body of a patient, including but not limited to the limbs, the trunk, the abdomen, the head and/or the neck could be equipped with at least one sensor network 12c comprising at least two sensors for measuring any type of body movement.

Figure 8C:
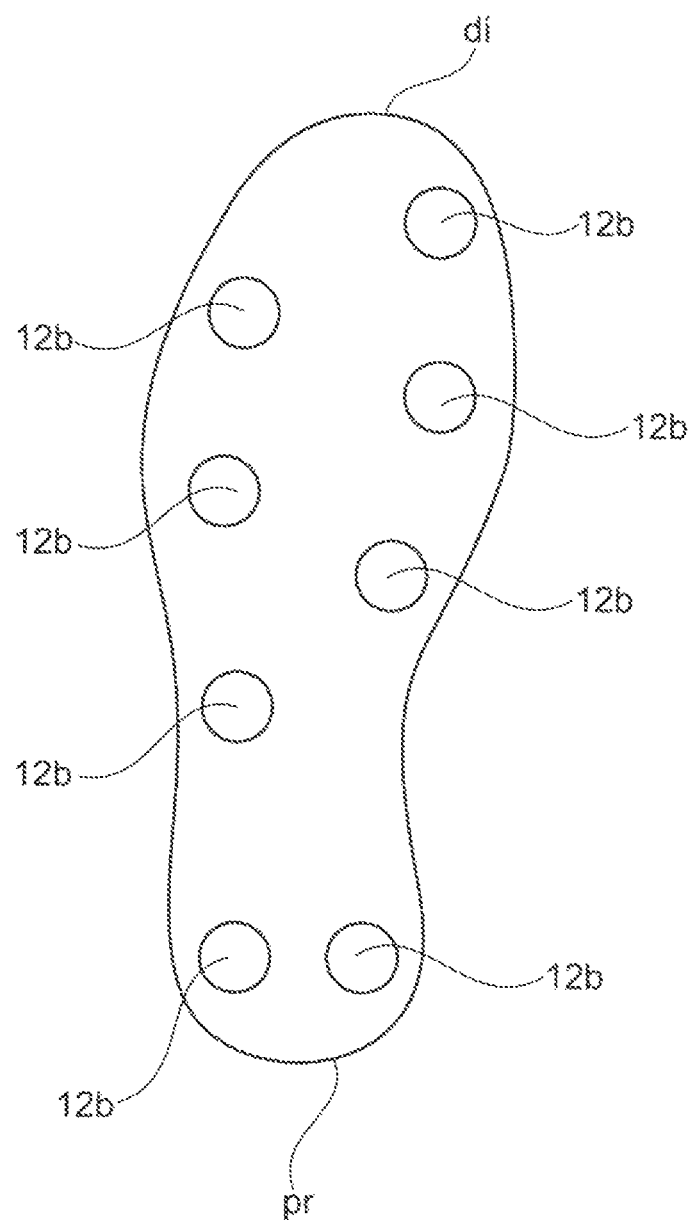
FIG. 8C a perspective view of a sensor insole according to the present invention.

FIG. 8C shows a perspective view of a sensor insole according to the present invention.

In this embodiment, according to the control system 10 disclosed in FIG. 7, various sensors 12 are integrated into a sensor insole 100 for a shoe S of a patient.

In this embodiment, the sensors 12 are pressure sensors 12b.

In particular, eight pressure sensors 12b are incorporated in a sensor insole 100 for a shoe S of a patient P.

In particular, the eight pressure sensors 12b are distributed from the distal end di of a sensor insole 100 to the proximal end pr of a sensor insole 100 for a shoe S of a patient.

In particular, the eight pressure sensors 12b are distributed along the heel area, the metatarsal area, and the toe area of the sensor insole 100.

In particular, two pressure sensors 12b are placed in the heel area, two pressure sensors 12b are placed in the toe area and four pressure sensors 12b are placed in the metatarsal area of the sensor insole 100.

In general, both shoes S of a patient P could be equipped with sensor insoles 100.

The sensor insoles 100 provide a precise map of the foot force.

In particular, the pressure sensors 12b in the sensor insole 100 provide a precise description of the gait phase and cadence, swing, stance, toe-off, midswing, heel strike, flat foot, midstance and/or heel-off can be identified for one foot by analyzing sensor data obtained from one sensor insole 100 of a shoe S.

The same events and parameters can be identified for the other foot of the patient P by using a second sensor insole 100.

By combining signals of sensor insoles 100 of both feet of a patient P, together with the gait phase and cadence of the stimulation input, a reliable gait phase and cadence estimate can be provided.

The sensor stream is transmitted to the controller 14 according to the disclosure of FIG. 7.

In one embodiment, alternative placements of the eight pressure sensors 12b in a sensor insole 100 could be possible.

However, it could be also possible that 1-7 or more than 8 pressure sensors 12b are integrated in a sensor insole 100 of a shoe S of a patient P.

It could also be possible that the sensor insole 100 itself is a pressure sensor 12b.

Figure 8D:
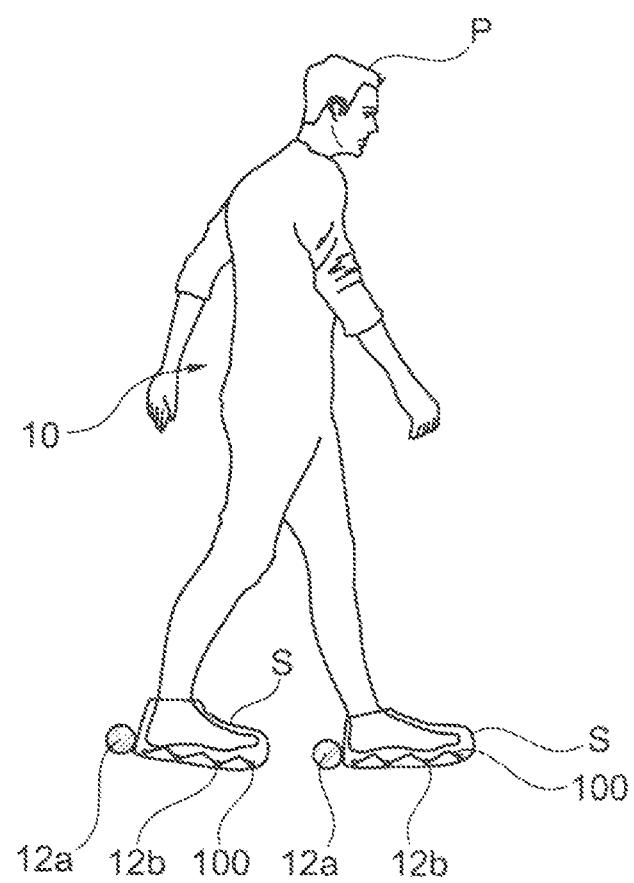
FIG. 8D a perspective view of a patient equipped with the control system disclosed in FIG. 7 comprising one IMU and one pressure insole for each foot according to the present invention.

FIG. 8D shows a perspective view of a patient equipped with the control system disclosed in FIG. 7 comprising one IMU and one pressure insole for each foot of the patient according to the present invention.

In this embodiment, a patient P is equipped with the control system 10 disclosed in FIG. 7 including one IMU 12a placed on the left shoe S and one IMU 12a placed on the right shoe S of a patient P as disclosed in FIG. 8A and one sensor insole 100 as disclosed in FIG. 8C for the left shoe S of the patient P and one sensor insole 100 as disclosed in FIG. 8C for the right shoe of the patient P.

Accordingly, the sensor insoles 100 for both shoes of the patient P comprise eight pressure sensors 12b (only exemplarily shown in FIG. 8D).

Alternatively, a patient P could be equipped with the control system 10 described in FIG. 7 including one IMU 12a and one respective sensor insole 100 for the left or the right foot.

In another embodiment, the IMU and/or the sensor insole can be replaced by another type of sensor 12 including but not limited to e.g. a piezo element.

In this embodiment, it could be possible that the piezo element is integrated in wearables like e.g. a sock, a knee sock, tights, a shoe.

Note that the example control and estimation routines included herein can be used with various system configurations. The control methods and routines disclosed herein may be stored as executable instructions in non-transitory memory and may be carried out by a control system 10 e.g. as a part of the controller 14 in combination with the sensors 12, the EES-Module 30 and/or he FES-Module 40, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the controller 14, where the described actions are carried out by executing the instructions in a control system 10 including the various hardware components.

Figure 9:
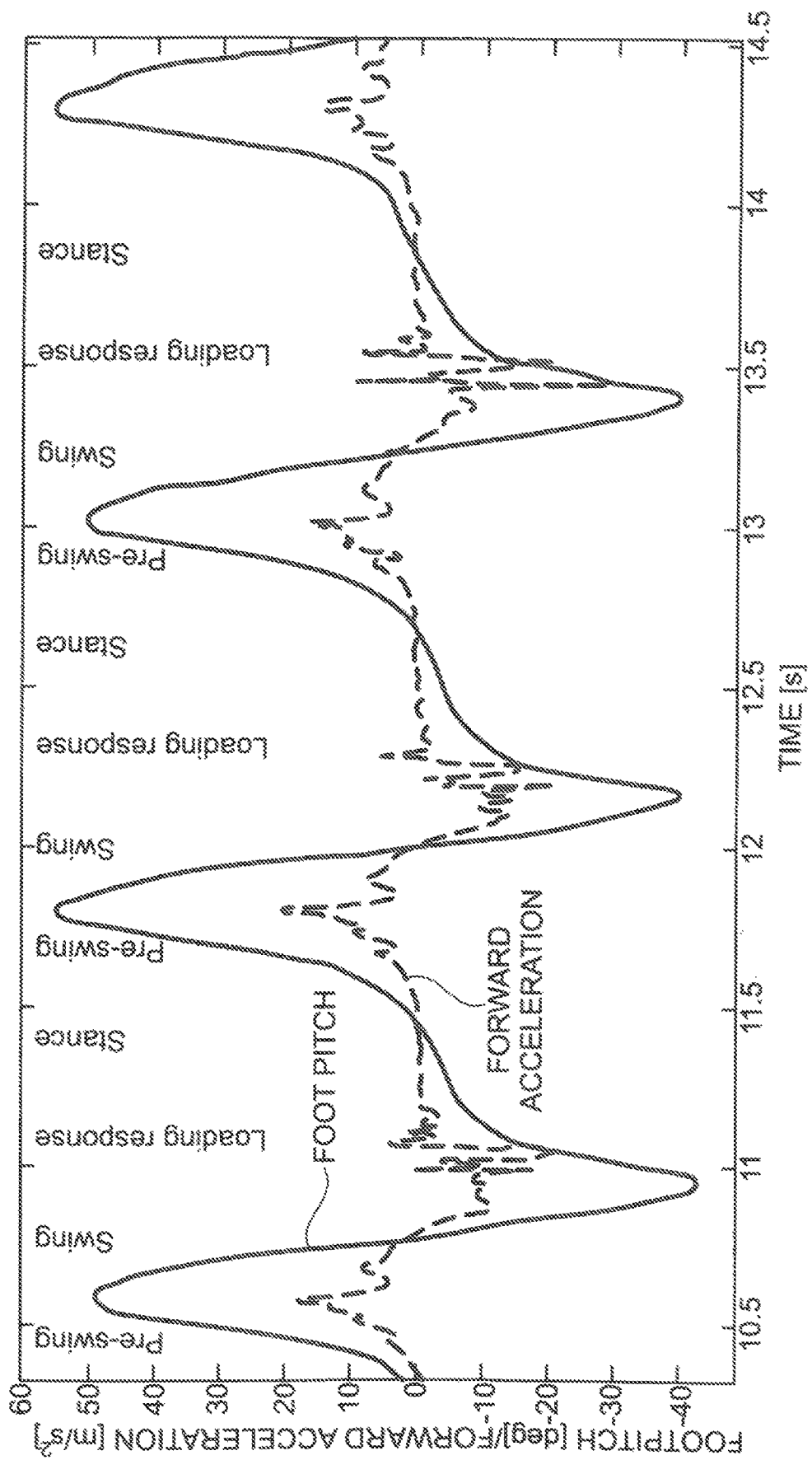
FIG. 9 a schematical diagram of food pitch/forward acceleration of a patient P equipped with the control system disclosed in FIG. 7.

FIG. 9 shows a schematic diagram of food pitch/forward acceleration of a patient P equipped with the control system disclosed in FIG. 7.

Here, the patient P is equipped with one IMU 12a per foot.

Alternatively, the patient P could be equipped with the control system 10 described in FIG. 7 including one IMU 12a and one respective sensor insole 100 for the left or the right foot.

In another embodiment, the patient could be equipped with two or more IMUs 12a per foot.

Further, the IMU 12a and/or the sensor insole 100 can be replaced by another type of sensor 12 including but not limited to e.g. a piezo element.

In this embodiment, it could be possible that the piezo element is integrated in wearables like e.g. a sock, a knee sock, tights, a shoe.

The foot pitch (degree) and forward acceleration (meter per $s^2$) of the right foot of a patient P equipped with the control system 10 disclosed in FIG. 7 during walking is shown.

From these signals, clearly the cadence, pre-swing, swing, loading response and stance can be identified.

The same events and parameters can be identified for the left foot.

As walking is a periodic motion, all measured signals are also periodic.

By combining gait phase and cadence information of both feet of the patient together with the gait phase and cadence of the stimulation input, a reliable gait phase and cadence estimate can be provided.

Note that gait can vary a lot between different patients P as well as for a single patient P for different walking speeds and different assistive devices (body-weight support, walker, crutches, etc.).

Especially for impaired gait, not all gait events are always present.

Hence, it is always possible to estimate the cadence by extracting the base frequency of the measured signals.

Moreover, machine-learning methods can be used to adapt the gait phase estimation to the specific gait of the patient P.

The level of agreements and discrepancies between motion of the left and right foot, and the stimulation input, can be used to give an indication of the gait phase estimation reliability, e.g., the measured cadence of the left foot should be equal to the measured cadence of the right foot and the cadence of the provided stimulation, and the left foot and right foot should be (roughly) in anti-phase.

In the control loop also use can made of the realization that the feet do not move independently from each other but are connected mechanically via the hip and on neural level via the spinal cord.

In particular, inhibitory reflex circuits in the spinal cord modulate neural firing rates (and hence modulate recruitment of motor neurons through EES).

Note that the example control and estimation routines included herein can be used with various system configurations. The control methods and routines disclosed herein may be stored as executable instructions in non-transitory memory and may be carried out by a control system 10 e.g. as a part of the controller 14 in combination with the one or more sensors 12, the IPG 18, the lead 20, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the controller 14, where the described actions are carried out by executing the instructions in a control system 10 including the various hardware components.

REFERENCES

10 control system
12 sensor
12*a* inertial measurement unit (IMU)
12*b* pressure sensor
12*c* sensor network
14 controller
18 implantable pulse generator (IPG)
20 lead
22 electrode module
22*a* electrode for FES
22*b* electrode for EES
30 CNS-Stimulation Module, EES-Module
40 PNS-Stimulation Module, FES-Module
100 sensor insole
pr proximal region of the foot or insole
di distal region of the foot or insole
P Patient
S Shoe
CMB custom muscle blocks
EES Epidural Electrical Stimulation
FES Functional Electrical Stimulation
FMB functional muscle block
WL wireless link
WSN wireless network, connection
TEL connection, telemetry line
LVLat left vastus lateralis
RVLat right vastus lateralis
Lll left iliopsoas
Rll right iliopsoas
LRF left rectus femoris
RRF right rectus femoris
LST left semitendinosus
RST right semidentinosus
LTA left tibialis anterior
RTA right tibialis anterior
LMG left medial gastrocnemius
RMG right medial gastrocnemius
LSol left soleus
RSol right soleus
LFHL left flexor halluces longus
RFHL right flexor halluces longus

The invention claimed is:

1. A control system for a movement reconstruction and/or restoration for a patient with a neurological disorder, comprising:
a CNS-Stimulation Module comprising an EES-Module configured to provide a CNS-Stimulation to a patient; and/or a PNS-Stimulation Module comprising an FES-Module, configured to provide a PNS-Stimulation to the patient;
a controller configured to control one or more of the CNS-Stimulation Module and the PNS-Stimulation Module;
at least one sensor configured to measure at least one parameter indicative of the movement of at least one limb or part of a limb or the trunk or the head of the patient; and
a pre-warning module configured to provide a pre-warning signal indicative of providing an upcoming stimulation event, the pre-warning signal is configured to assist the patient to coordinate the patient's voluntary control of the movement and the upcoming stimulation event;
wherein the pre-warning signal acts in a sub-motor threshold region;
wherein the controller arranges and controls one or more of the CNS-Stimulation Module and the PNS-Stimulation Module using the at least one sensor to predict the intended movement of the patient.

2. The control system of claim 1, wherein the control system further comprises an electrode module, which is configured and arranged to stimulate a patient locomotor system.

3. The control system of claim 2, wherein the electrode module comprises at least one electrode, which is configured and arranged to stimulate the patient locomotor system, wherein the electrode is attached to or arranged at the limb of part of the limb or foot or CNS or spinal circuits, or dorsal roots.

4. The control system of claim 3, wherein each limb is targeted or targetable with at least one electrode.

5. The control system of claim 4, wherein the electrode is configured and arranged for limb cramp stimulation to release cramp or detection of limb cramp.

6. The control system of claim 1, wherein the sensor is configured and arranged to be inserted or integrated into or onto one or more of an exoskeleton, tights, a belt, straps, a stretching band, a knee sock, a sock, and a shoe of the patient.

7. The control system of a claim 6, wherein the sensor is configured and arranged to be inserted or arranged in the shoe or into the sole or into the insole of the shoe of the patient.

8. The control system of claim 1, wherein the controller is configured and arranged to adapt the CNS-Stimulation provided by the CNS-Stimulation Module and the PNS-Stimulation provided by the PNS-Stimulation Module based on data provided by the sensor.

9. The control system of claim 1, wherein at least one sensor is arranged at each limb or part of a limb of the patient.

10. The control system of claim 1, wherein the sensor is at least one of an inertial measurement unit (IMU), an optical sensor, a camera, a piezo element, a velocity sensor, an accelerometer, a magnet sensor, a torque sensor, a pressure sensor, a displacement sensor, a contact sensor, an EMG measurement unit, a goniometer, a magnetic field sensor, a hall sensor and/or a gyroscope and/or a motion tracking video camera, or a infra-red camera.

11. The control system of claim 1, comprising both the CNS-Stimulation Module and the PNS-Stimulation Module.

* * * * *